US006813017B1

(12) United States Patent
Hoffman et al.

(10) Patent No.: US 6,813,017 B1
(45) Date of Patent: Nov. 2, 2004

(54) APPARATUS AND METHOD EMPLOYING INCOHERENT LIGHT EMITTING SEMICONDUCTOR DEVICES AS PARTICLE DETECTION LIGHT SOURCES IN A FLOW CYTOMETER

(75) Inventors: Robert A. Hoffman, Livermore, CA (US); Eric S. Chase, Walnut Creek, CA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 141 days.

(21) Appl. No.: 09/691,155

(22) Filed: Oct. 19, 2000

Related U.S. Application Data

(60) Provisional application No. 60/160,498, filed on Oct. 20, 1999.

(51) Int. Cl.[7] ............................. G01J 3/30; G01N 21/25
(52) U.S. Cl. ...................... 356/317; 356/410; 356/417
(58) Field of Search .................. 356/303, 317–318, 356/337–339, 410, 417, 72, 73; 250/458.1–461.2

(56) References Cited

U.S. PATENT DOCUMENTS

| | | | |
|---|---|---|---|
| 3,886,363 A | | 5/1975 | Ohnishi et al. |
| 3,918,812 A | | 11/1975 | Holm |
| 3,960,449 A | | 6/1976 | Carleton et al. |
| 4,006,360 A | | 2/1977 | Mueller |
| 4,306,805 A | * | 12/1981 | Arrington .................. 356/133 |
| 4,347,935 A | | 9/1982 | Merrill |
| 4,498,766 A | * | 2/1985 | Unterleitner ................. 356/73 |
| 4,573,796 A | | 3/1986 | Martin et al. |
| 4,667,830 A | | 5/1987 | Nozaki, Jr. et al. |
| 4,800,265 A | * | 1/1989 | Marzari et al. ............ 356/73.1 |

(List continued on next page.)

OTHER PUBLICATIONS

Robert A. Hoffman et al., Poster presented at ISAC XX, Montpellier, France, 2 pages, May, 2000.
Robert A. Hoffman et al., "Light Emitting Diodes as Light Sources for Flow Cytometry" Published Abstract #6109 in Cytometry Supplement 10: 163 and Figs. 1–8, 2 pages, May, 2000.

(List continued on next page.)

Primary Examiner—F. L. Evans
Assistant Examiner—Kara Geisel
(74) Attorney, Agent, or Firm—Douglas A. Petry

(57) ABSTRACT

An apparatus and method for examining particles in a flow stream of a flow cytometer, employing incoherent light sources, such as light emitting diodes (LEDs), and detectors. The light emitting diodes operate as the excitation light sources and emit light toward said flow stream, and the detectors detect light, in particular, fluorescent light, emanating from the particles in response to the excitation light striking the particles. A controller controls each of the light emitting diodes to emit their excitation light for a predetermined period during which the excitation light radiates onto particles of interest. The controller evaluates the detected light to ascertain characteristics of the particles, such as particle size, density and granularity. The apparatus and method can further employ one or more coherent and homogenous light emitting devices, such as a laser, as an additional excitation light source. The detectors can detect the LED-excited fluorescence or the laser-excited fluorescence from the particles, and the controller can evaluate both types of detected light to ascertain characteristics of the particles. Furthermore, the controller can control the LEDs to operate in a pulsed manner, which can be synchronized with the detection of the laser-excited fluorescence or light scatter. In addition, a substantially opaque panel having one or more slits can be positioned at the image plane upon which an image of the flow stream is projected, so that the slits will allow only a portion of the image to pass to the detector associated with the panel.

2 Claims, 22 Drawing Sheets

U.S. PATENT DOCUMENTS

| | | | | |
|---|---|---|---|---|
| 4,857,735 | A | * | 8/1989 | Noller .................. 250/339.07 |
| 4,989,978 | A | | 2/1991 | Groner |
| 5,185,265 | A | | 2/1993 | Steen et al. |
| 5,317,162 | A | * | 5/1994 | Pinsky et al. ............... 356/317 |
| 5,434,081 | A | | 7/1995 | Maekawa |
| 5,464,581 | A | | 11/1995 | van den Engh |
| 5,483,469 | A | | 1/1996 | Van den Engh et al. |
| 5,528,045 | A | * | 6/1996 | Hoffman et al. ............ 356/317 |
| 5,563,070 | A | * | 10/1996 | Yamamoto et al. ........... 356/73 |
| 5,596,401 | A | * | 1/1997 | Kusuzawa .................. 356/336 |
| 5,602,039 | A | | 2/1997 | Van den Engh |
| 5,643,796 | A | | 7/1997 | Van den Engh et al. |
| 5,674,698 | A | * | 10/1997 | Zarling et al. .......... 422/82.05 |
| 5,700,692 | A | | 12/1997 | Sweet |
| 5,767,953 | A | * | 6/1998 | McEwan ................... 356/5.01 |
| RE35,868 | E | * | 8/1998 | Kosaka ...................... 356/336 |
| 6,046,807 | A | | 4/2000 | Chandler .................. 356/318 |
| 6,121,053 | A | * | 9/2000 | Kolber et al. ............. 250/458.1 |
| 6,139,800 | A | | 10/2000 | Chandler ................ 422/82.08 |
| 6,197,593 | B1 | * | 3/2001 | Deka et al. ................... 436/63 |
| 6,366,354 | B1 | | 4/2002 | Chandler .................. 356/318 |
| 6,411,904 | B1 | | 6/2002 | Chandler .................... 702/21 |

OTHER PUBLICATIONS

R.C. Leif et al., "Electronic Cell–Volume Analysis by Use of the AMAC I Transducer", *Clinical Chemistry*, vol. 19, No. 8, pp. 853–870, 1973.

David B. Kay et al., Laser Stroboscopic Photography Technique for Cell Orientation Studies in Flow, *The Journal of Histochemistry and Cytochemistry*, vol. 24, No. 1, pp. 265–268, 1976.

R. A. Thomas et al., "Computer–Based Electronic Cell Volume Analysis with the AMAC II Transducer", *The Journal of Histochemistry and Cytochemistry*, vol. 22, No. 7, pp. 626–641, 1974.

Harald B. Steen et al., "Pulse Modulation of the Excitation Light Source Boosts the Sensitivity of an Arc Lamp–Based flow Cytometer", *Cytometry*, vol. 14, No. 2, pp. 115–122, 1993.

* cited by examiner

APPARATUS AND METHOD EMPLOYING INCOHERENT LIGHT EMITTING SEMICONDUCTOR DEVICES AS PARTICLE DETECTION LIGHT SOURCES IN A FLOW CYTOMETER

The present application claims benefit from U.S. Provisional Patent Application Ser. No. 60/160,498 filed Oct. 20, 1999, the entire content of which is incorporated herein by reference.

CROSS-REFERENCE TO RELATED APPLICATIONS

Related subject matter is disclosed in a copending U.S. Patent Application of Pierce O. Norton entitled "Apparatus and Method for Verifying Drop Delay in a Flow Cytometer", Ser. No. 09/346,692, filed Jul. 2, 1999, the entire content of which is incorporated herein by reference.

BACKGROUND OF THE INVENTION

1. Field of the Invention

The present invention relates to an apparatus and method employing incoherent light sources, in particular, light emitting diodes, as excitation light sources in a flow cytometer. More particularly, the present invention relates to an apparatus and method employing light emitting diodes as excitation light sources for emitting light toward a particle stream in a flow cytometer to cause particles or cells of interest in the stream to fluoresce so that characteristics of the particles or cells can be examined based on the detected fluorescence.

2. Description of the Related Art

Flow cytometers known in the art are used for analyzing and sorting particles in a fluid sample, such as cells of a blood sample or particles of interest in any other type of biological or chemical sample. A flow cytometer typically includes a sample reservoir for receiving a fluid sample, such as a blood sample, and a sheath reservoir containing a sheath fluid. The flow cytometer transports the particles (hereinafter called "cells") in the fluid sample as a cell stream to a flow cell, while also directing the sheath fluid to the flow cell.

Within the flow cell, a liquid sheath is formed around the cell stream to impart a substantially uniform velocity on the cell stream. The flow cell hydrodynamically focuses the cells within the stream to pass through the center of a laser beam. The point at which the cells intersect the laser beam, commonly known as the interrogation point, can be inside or outside the flow cell. As a cell moves through the interrogation point, it causes the laser light to scatter. The laser light also excites components in the cell stream that have fluorescent properties, such as fluorescent markers that have been added to the fluid sample and adhered to certain cells of interest, or fluorescent beads mixed into the stream.

The flow cytometer further includes an appropriate detection system consisting of photomultiplier tubes, photodiodes or other light detecting devices, which are positioned to collect light from the intersection point. The flow cytometer analyzes the detected light to measure physical and fluorescent properties of the cell. The flow cytometer can further sort the cells based on these measured properties.

Known flow cytometers similar to the type described above are described, for example, in U.S. Pat. Nos. 3,960,449, 4,347,935, 4,667,830, 5,464,581, 5,483,469, 5,602,039, 5,643,796 and 5,700,692, the entire contents of each patent being incorporated by reference herein. Other types of known flow cytometer, are the FACSVantage™, FACSort™, FACSCount™, FACScan™ and FACSCalibur™ systems, each manufactured by Becton Dickinson and Company, the assignee of the present invention.

Known flow cytometers, such as those mentioned above and described in the patents cited above, usually employ lasers as the light sources that emit light beams which are directed toward the cell stream to excite particles of interest in the cell stream to cause those particles to fluoresce. Although lasers are generally effective in producing focused beams which are of sufficient intensity to excite the particles of interest to provide detectable fluorescence, the use of lasers can have some drawbacks. For example, the types of lasers employed in many known flow cytometers are very expensive, and thus increase the overall cost of the system.

Also, because the lasers emit very high intensity light, stray light from one of the laser beams can interfere with the fluorescent light emanating from the particles of interest caused by excitation from another laser beam, thus adversely affecting fluorescence measurements. In an attempt to eliminate this problem, a flow cytometer including multiple lasers can be configured to operate the lasers or other light sources, such as arc lamps, in an intermittent or pulsed manner as described, for example, in U.S. Pat. No. 4,573,796 to Martin et al., U.S. Pat. No. 5,185,265 to Steen et al. and U.S. Pat. No. 4,006,360 to Mueller, and in a publication by H. B. Steen and O. J. Sorenson entitled "Pulse Modulation of the Excitation Light Source Boosts the Sensitivity of an Arc Lamp-Based Flow Cytometer", Cytometry, Vol. 14, No. 2, pages 115–22 (1993), the entire content of these patents and this publication being incorporated herein by reference. This strobing or pulsing technique is further described in a publication by D. B. Kay and L. L. Wheeless, Jr. entitled "Laser Stroboscopic Photography—Technique for Cell Orientation Studies in Flow", The Journal of Histochemestry and Cytochemistry, Vol. 24, No. 1, pages 265–268 (1976), in a publication by R. C. Leif and R. A. Thomas entitled "Electronic Cell-Volume Analysis by Use of the AMAC I Transducer", Clinical Chemistry, Vol. 19, No. 8, pages 858–70 (1973), and in a publication by R. A. Thomas, B. F. Cameron and R. C. Lief entitled "Computer-Based Electronic Cell Volume Analysis with the AMAC II Transducer", The Journal of Histochemestry and Cytochemistry, Vol. 22, No. 7, pages 626–41 (1974), the entire contents of each of these publications being incorporated herein by reference.

The techniques described in the documents referenced above have been only partially successful, because the types of lasers and arc lamps having characteristics suitable for use in flow cytometry experience difficulty in being turned on and off rapidly for short periods of time. Therefore, a need exists for an improved system and method which enables a flow cytometer to obtain more accurate measurements while also decreasing the overall size and cost of the instrument.

SUMMARY OF THE INVENTION

An object of the present invention is to provide a system and method employing improved excitation light sources for use in a flow cytometer.

Another object of the present invention is to provide a system and method employing light emitting diodes as excitation light sources for use in a flow cytometer to reduce the overall cost of the flow cytometer.

A further object of the present invention is to provide a system and method capable of effectively pulsing the excitation light sources in a flow cytometer to minimize interference between the light emitted by multiple light sources while also decreasing power consumption and increasing the life of the light sources.

These and other object of the present invention are substantially achieved by providing an apparatus and method for examining particles in a flow stream of a flow cytometer, employing incoherent light sources, including incoherent light emitting semiconductor devices such as light emitting diodes (LEDs), and detectors. The light emitting diodes are adapted to operate as the excitation light sources and emit light toward the flow stream, and the detectors detect light, in particular, fluorescent light, emanating from the particles in response to the excitation light striking the particles. The apparatus and method further employs a controller which is adapted to control each of the light emitting diodes to emit their excitation light for a predetermined period during which the excitation light radiates onto particles of interest. The controller evaluates the detected light to ascertain characteristics of the particles, such as particle size, density and granularity. The apparatus and method can further employ one or more coherent light emitting devices, such as a laser, as an additional excitation light source. The detectors can be adapted to detect the LED-excited fluorescence or the laser-excited fluorescence from the particles, and the controller can evaluate both types of detected light to ascertain characteristics of the particles. Furthermore, the controller can control the LEDs to operate in a pulsed manner, which can be synchronized with the detection of the laser-excited fluorescence.

BRIEF DESCRIPTION OF THE DRAWINGS

The various objects, advantages and novel features of the present invention will be more readily appreciated from the following detailed description when read in conjunction with the accompanying drawings, in which.

DETAILED DESCRIPTION OF THE PREFERRED EMBODIMENTS

Figure 1:
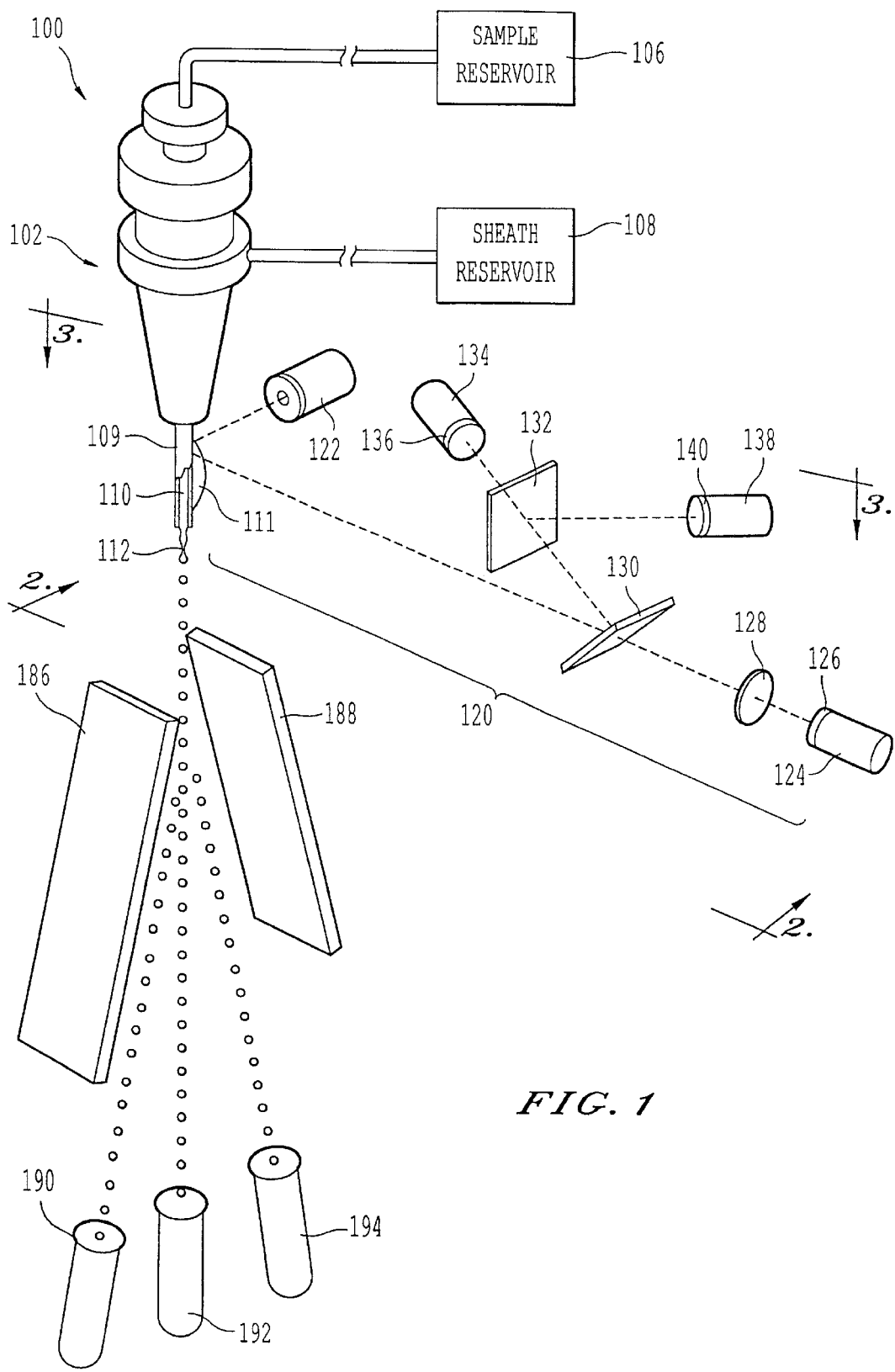
FIG. 1 is a schematic perspective view of a flow cytometer employing an apparatus according to an embodiment of the present invention.
Figure 2:
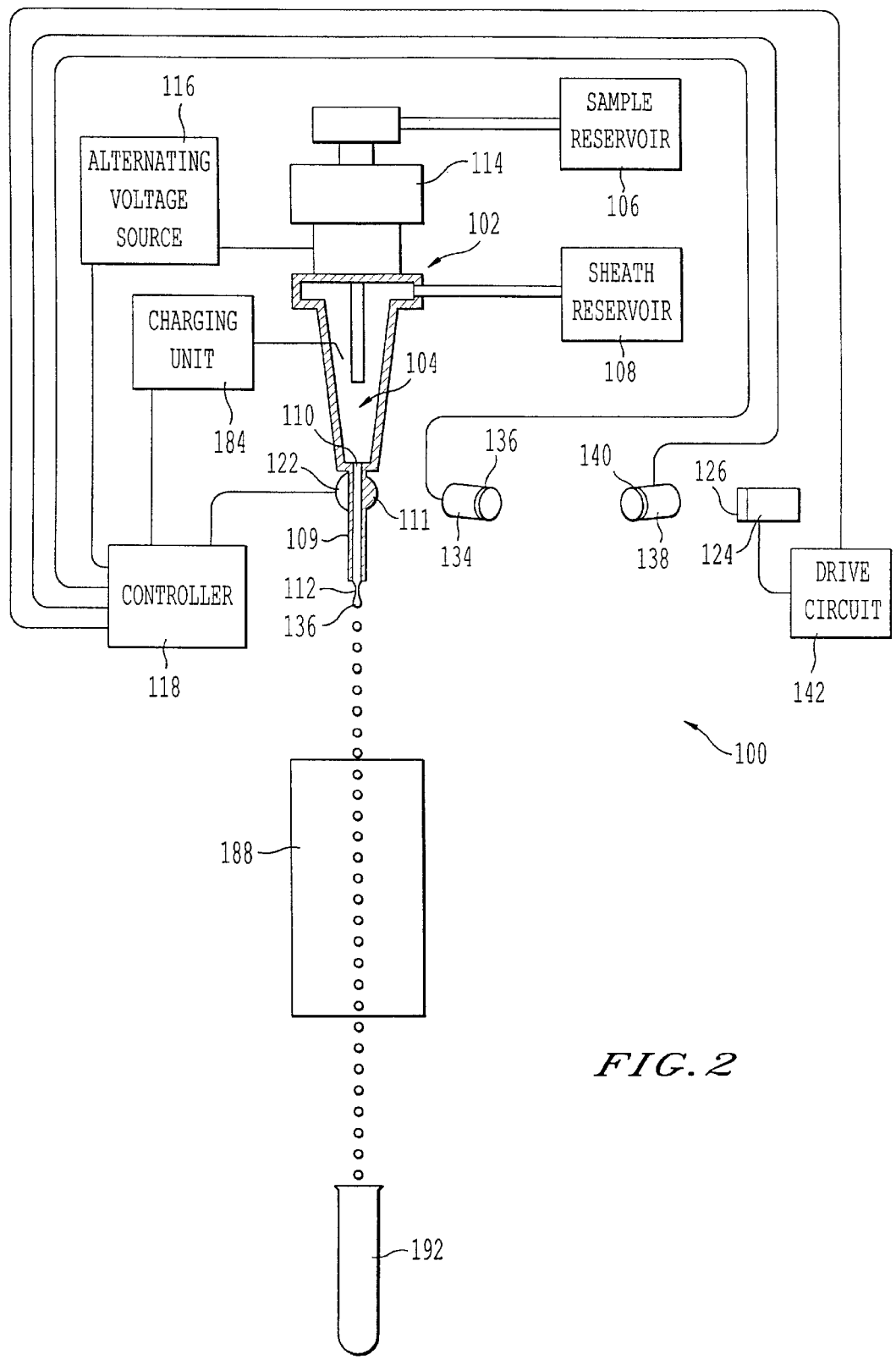
FIG. 2 is a schematic illustration of a front view of a portion of the flow cytometer shown in FIG. 1.
Figure 3:
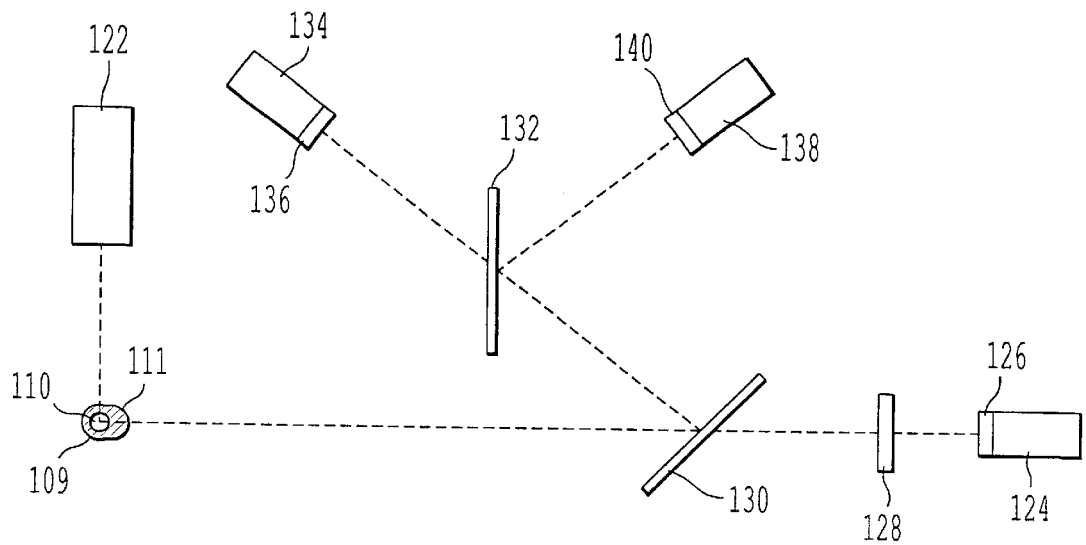
FIG. 3 is a view of a portion of the flow cytometer as taken along lines 3—3 in FIG. 1.

A flow cytometer 100 employing an embodiment of the present invention is illustrated in FIGS. 1–3. As discussed in the background section above, the flow cytometer 100 includes a nozzle 102 having a flow cell 104 therein. The flow cytometer further includes a sample reservoir 106 for receiving a fluid sample, such as a blood sample, sperm sample or other particle sample, and sheath reservoir 108 containing a sheath fluid. The flow cytometer transports the cells in the fluid sample in the cell stream to the flow cell 104, while also directing the sheath fluid to the flow cell 104.

Figure 4:
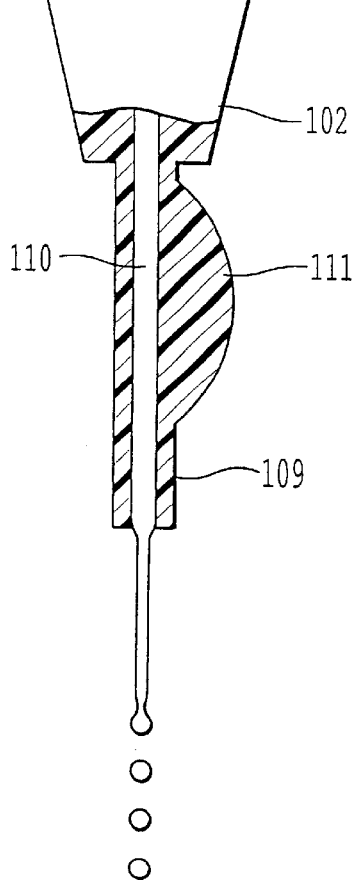
FIG. 4 is a detailed cross-sectional view of an example of the capillary and immersion lens arrangement of the nozzle in the flow cytometer show in FIGS. 1–3.

Within the flow cell 104, the sheath fluid surrounds the cell stream, and the combined sheath fluid and cell stream exits the flow cell 104 via an opening in a capillary 109 as a sample stream 110. The opening in the capillary 109 can have a diameter of, for example, 50 $\mu$m, 70 $\mu$m, 100 $\mu$m, or any other suitable diameter. Typically the exit opening is constricted to be smaller than the upstream portion of the capillary. As shown in more detail in FIG. 4, the light collection from the capillary 109 includes an immersion lens arrangement 111, the purposes of which are described in more detail below. The immersion lens arrangement 111 can include, for example, a matching fluid such as silica based gel which acts as an interface between the capillary 109 and immersion lens arrangement 111 to substantially eliminate the incidence of refraction between capillary 109 and the immersion lens arrangement 111. The immersion lens arrangement 111 can alternatively be made integral with the capillary 109. The immersion lens typically has multiple optical elements to provide a compound lens with adequate magnification and minimal aberrations. Only the first element of the compound lens is shown the schematic FIG. 1.

Also, although FIGS. 1–3 show the flow cell 104 has having a capillary 109, the embodiments of the present invention described herein can be employed with a system 100 having a flow cell 104 that produces a stream-in-air flow stream as described, for example, in U.S. patent application Ser. No. 09/346,692 referenced above. In such an arrangement, the immersion lens arrangement 111 is positioned with respect to the flow stream 109 in air to focus light onto the flow stream and to collect light from the flow stream.

As illustrated, due to characteristics of the sheath fluid, such as surface tension and the like, the sample stream remains intact until breaking off into droplets at the droplet break off point 112, which is at a certain distance from the opening at the end of capillary 109. The distance from the opening in the capillary 109 at which the droplet break off point 112 occurs, and the frequency or rate at which the droplets are formed, are governed by the fluid pressure, as well as the amplitude and frequency of oscillation of oscillating device 114 which can be, for example, a piezoelectric element.

As shown in FIG. 2, the oscillating device 114 is connected to an alternating voltage source 116 whose output voltage amplitude, frequency and phase is controlled by a controller 118 which can be, for example, a microprocessor or any other suitable controlling device. The amplitude of the alternating voltage signal output by alternating voltage source 116 can be increased or decreased by controller 118 to increase or decrease the distance form opening 110 at which the droplet break off 112 occurs. Likewise, the frequency of the alternating voltage signal output by alternating voltage source 116 can be increased or decreased by controller 118 to increase or decrease the rate at which droplets of sample fluid are formed at the droplet break off point 112.

The flow cytometer 100 in this example includes a cell evaluation assembly 120 which includes a laser 122, an LED assembly 124 having a lens 126, an optional filter 128, a first and second dichroic mirrors 130 and 132, a first detector 134 having a filter 136, and a second detector. 138 having a filter 140. The laser 124 can be any known type of laser, such as a diode laser, semiconductor laser, or the like, which is controlled by controller 118 to emit laser light which radiates onto flow stream 110 as described in more detail below. For example, the laser 122 can be a red diode laser emitting laser light having a wavelength of 635 nm, an argon laser emitting blue light having a wavelength of about 488 nm, or a YAG laser emitting green light having a wavelength of 532 nm. The detectors 134 and 138 can each be photomultiplier tubes (PMTs) or any other suitable type of light detecting device. The detectors 134 and 138 and, in particular, their respective filters 136 and 140 are positioned within the path of the light exiting from the immersion lens arrangement 111 so that the immersion lens arrangement 111 can focus an image of the sample stream 110 onto the filters 136 and 140 as described in more detail below. In this example, filter 136 permits fluorescent light emitted from the cells which have been excited by light from LED assembly 124 to pass to detector 134, and filter 140 permits fluorescent light emitted from the cells which have been excited by light from laser 122 to pass to detector 138.

The LED assembly 124 includes an LED 125 (see FIGS. 5–7) which emits light that is focused by lens 126 onto flow stream 110. In this example, the light emitted by laser 124 radiates onto flow stream 110 at a point which is about 100 microns upstream of the point at which the light emitted by LED 125 radiates onto flow stream 110. The light emitted by LED 125 has an appropriate wavelength to cause cells of interest that have been treated with an appropriate stain to fluoresce as described in more detail below. For example, the LED assembly 124 can include an LED that emits ultraviolet (UV) light having a wavelength of about 370 nm. Alternatively, LED assembly 124 can include an LED that emits blue light having a wavelength within the range of about 430 nm to about 470 nm, an LED that emits green light having a wavelength of about 520 nm, or an LED that emits light having a wavelength of about 635 nm. Each LED can be, for example, a GaN based LED manufactured by Nichia which has an emission surface of about 0.3 mm×0.3 mm square, from which is emitted light having an output power within the range of about 1 mW to about 5 mW. Typically, the brightness of each of these LEDs is about 100 times less intense, in terms of power per unit area, than a laser beam with the same power focused to a typical 20 $\mu$m×60 $\mu$m spot as in known flow cytometers.

It is noted that cell evaluation assembly 120 can include no laser, or any number of lasers, dichroic mirrors, detectors and LED assemblies, which can be arranged to evaluate different types of particles and different characteristics of the cells, such as size, complexity and granularity, as discussed in more detail below. The cell evaluation assembly 120 can also include other types of continuous wave light emitting devices, such as arc lamps, in place of or in addition to a laser. Moreover, although only a single cell evaluation assembly 120 is shown in FIG. 1 for exemplary purposes, the flow cytometer 100 can employ any number of cell evaluation assemblies having one or more lasers, one or more LED assemblies, one or more dichroic mirrors, and one or more detectors, which can be similar to the components shown in particle evaluation assembly 120.

As shown in FIG. 2, controller 118 controls laser 122, detectors 134 and 138, and an LED assembly driving circuit 142 as described in more detail below. Specifically, controller 118 can control the laser 122 to emit laser light as a continuous wave (CW) toward the sample stream 110. The controller 118 can further control the LED assembly driving circuit 142 to drive the LED of the LED assembly 124 in a CW or pulsed manner, as desired, and can control the detectors 134 and 138 to detect an image of the sample stream 110 created by the laser light or light from the LED as focused on the lenses 136 and 140. Detectors 126 and 128 each convert the light they receive into electrical signals which are interpreted by controller 118 as representing a characteristic of the cells in the sample fluid at a give sampling time.

Figure 5:
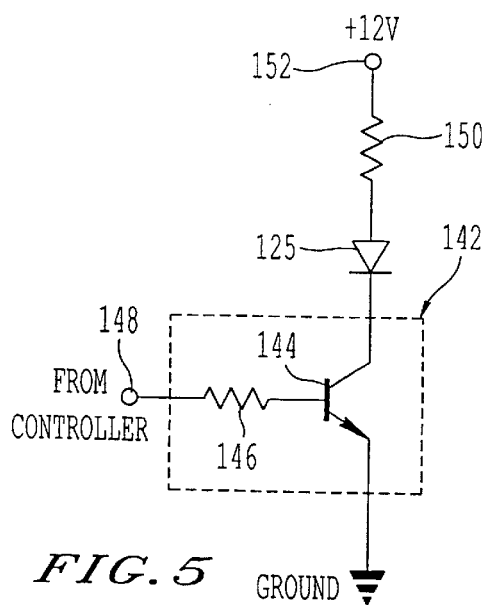
FIG. 5 is a circuit diagram illustrating an example of an LED driving circuit according to an embodiment of the present invention.
Figure 6:
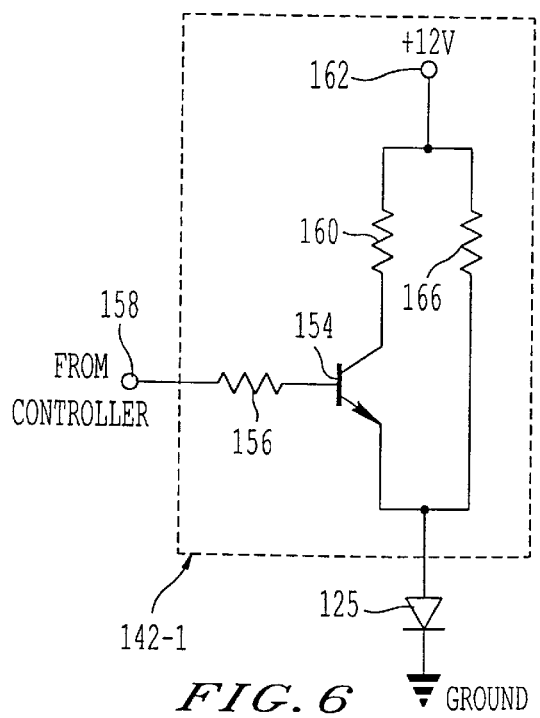
FIG. 6 is a circuit diagram illustrating another example of an LED driving circuit according to an embodiment of the present invention.
Figure 7:
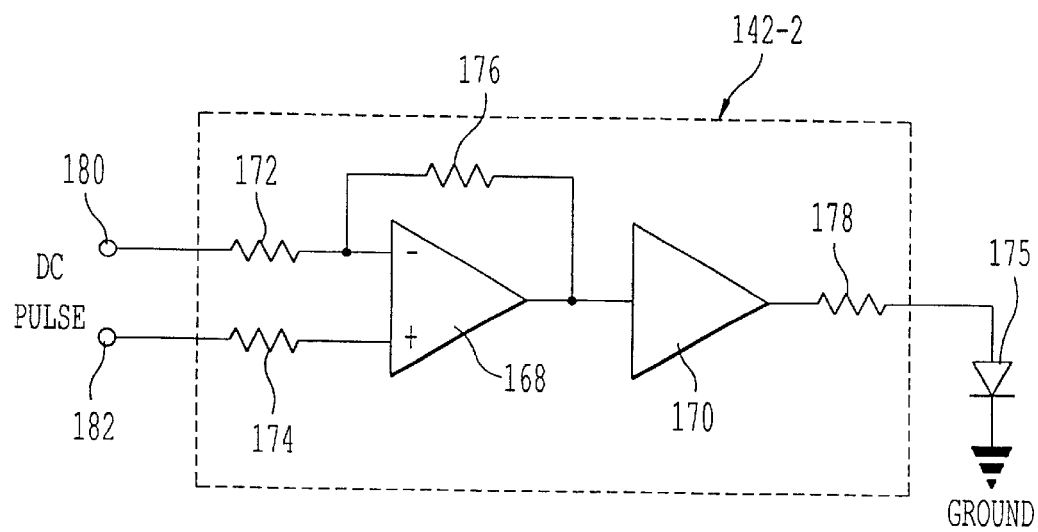
FIG. 7 is a circuit diagram illustrating a further example of an LED driving circuit according to an embodiment of the present invention.

FIGS. 5–7 illustrate examples of driving circuit 142. As shown in FIG. 5, driving circuit 142 can include a transistor 144, such as an npn transistor as shown or, alternatively, a pnp transistor, or any type of field effect transistor. A resistor 146, which can be a 2000 Ω resistor or a resistor of any suitable resistance value, is coupled at one end to the base of transistor 144 and at the other end to a terminal 148 which receives a signal from controller 118. The emitter of transistor 144 is coupled to ground, and the collector of transistor 144 is coupled to the cathode of an LED 125 of LED assembly 124 (see FIGS. 1–3). The LED assembly 124 can further include a resistor 150, which is coupled at one end to the anode of LED 150 and at the other end to a D.C. voltage source 152, such as a +12 D.C. voltage source. Resistor 150 can have a resistance within the range of about 10 Ω to about 500 Ω, or any other suitable resistance value. The signal provided from controller 118 to the base of transistor 144 via resistor 146 can be a continuous D.C. signal to maintain the transistor 144 in an active state for CW operation of LED 125. Alternatively, the signal can be a square wave pulse or any other suitable pulse wave which is capable of turning the transistor 144 off and on to thus turn the LED 125 off and on in a pulsed manner as described in more detail below.

The driving circuit can alternatively be configured as driving circuit 142-1 as shown in FIG. 6. Driving circuit 142-1 is similar to driving circuit 142 in that it includes a transistor 154, such as an npn transistor as shown or, alternatively, a pnp transistor, or any type of field effect transistor. A resistor 156, which can be a 2000 Ω resistor or a resistor of any suitable resistance value, is coupled at one end to the base of transistor 154 and at the other end to a terminal 158 which receives a signal from controller 118. The emitter of transistor 154 is coupled to the anode of LED 125 of LED assembly 124 (see FIGS. 1–3), and the cathode of an LED 125 is coupled to ground. The cathode of transistor 154 is coupled to one end of a resistor 160, which can be, for example, a 50 Ω resistor or can have any suitable resistance value. The other end of resistor 160 is coupled to a D.C. voltage source 162, such as a +12 D.C. voltage source.

The driving circuit 142-1 can further include a resistor 166 which has one end coupled to voltage source 162 and the other end coupled to the anode of diode 125. Resistor 166 can be a 500 Ω resistor, or can have any other suitable resistance value. As with driving circuit 142 described above, the signal provided from controller 118 to the base of transistor 154 via resistor 156 can be a continuous D.C. signal to maintain the transistor 154 in an active state for CW operation of LED 125. Alternatively, the signal can be a square wave pulse or any other suitable pulse wave which is capable of turning the transistor 154 off and on to thus turn the LED 125 off and on in a pulsed manner as described in more detail below.

As shown in FIG. 7, the driving circuit can be configured as driving circuit 142-2, which includes an operational amplifier 168, an inverter 170, and resistors 172, 174, 176 and 178. Resistors 172, 174, 176 and 178 can have values of 10,000 Ω, 10,000 Ω, 10,000 Ω, and 500 Ω, respectively, or any other suitable values. Resistor 172 is coupled at one end to an input terminal 180, and at the other end to the negative input of operation amplifier 168. Resistor 174 is coupled at one end to an input terminal 182, and at the other end to the positive input of operational amplifier 168. Resistor 176 is coupled at one end to the negative input of operational amplifier 168 and at the other end to the output of operational amplifier 168. The output of operational amplifier 168 is coupled to the input of inverter 170, and the output of inverter 170 is coupled via resistor 178 to the anode of diode 125 of diode assembly 124 (see FIGS. 1–3). In this arrangement, controller 118 can provide a continuous D.C. signal to terminal 180, so that the signal is applied to the negative input of operational amplifier 168 via resistor 172, to operate the LED in a CW mode. Alternatively, the controller 118 can provide a pulsed signal to the terminal 182, so that the pulsed signal is applied to the positive input of operational amplifier 168 via resistor 174 to operate the LED in a pulsed mode as described in more detail below.

As further shown in FIGS. 1–3, controller 118 can control a charging unit 184 to charge cells of interested in accordance with their detected characteristics, so that the cells can be sorted by deflection plates 186 and 188 which can be employed to sort cells of interest into different collection vessels 190, 192 and 194 as described in more detail in a copending U.S. patent application Ser. No. 09/346,692, referenced above.

The operation of the cell evaluation assembly 120 will now be described with reference to FIGS. 1–3 and 8–12. As can be appreciated by one skilled in the art, the cells in the sample contained in the sample reservoir 106 have been treated with a stain which will cause them to fluoresce when irradiated with light of a certain wavelength or within a certain wavelength range. Therefore, the type of stain used is therefore dependent on the type of laser 122 and LED 125 employed in the assembly 120. In other words, if the flow cytometer 100 includes several cell evaluation assemblies 120, each employing one or more lasers, LED assemblies and detectors, then the controller 118 will activate the appropriate laser(s) and/or LED(s) whose emitted light is within a wavelength range that will excite the particular stain of the particle of interest, and will activate the appropriate detector(s) whose filters will permit that light to pass to the detector.

For example, if the cells are stained with Hoechst 33342, Hoechst 33258 or 4', 6-Diamidino-2-phenylindole dihydrochloride (DAPI) stain, then the controller 118 can activate the laser 122 in the cell evaluation assembly 120 that emits, for example red light having a wavelength of about 635 nm, as well as the LED assembly 124 having an LED 125 that emits UV light having a wavelength of about 370 nm, in order to excite the stained cells to cause them to fluoresce. Filter 140 allows the UV light-excited fluorescence to pass for detection by the detector 138, while filter 136 allows the laser light to pass to detector 134 so that scattering of the laser light by the stained cells can be detected by detector 134.

In another example, the laser 122 can by a type of laser that emits 488 nm wavelength light so that multi-color analysis of the stained cells can be performed. In this event, the detector whose filter allows 488 nm wavelength to pass. However, if the cells are stained with SYTO16, or with Phycoerythrin, which is used as a fluorophore in immunofluorescence, or with other DNA dyes, then the controller 118 could activate a laser and/or LED assembly that emits blue light having a wavelength of about 475 nm, and detectors 134 and 138 would be associated with filters 136 and 140 which would allow blue light to pass. In this example, detector 134 would be detecting fluorescence emanating from the stained cells due to excitation by the laser light, instead of simply detecting light scattering.

As stated above, the controller 118 can control laser 122 to emit light in a CW manner. The light being emitted by laser 122 radiates onto flow stream 110 and will cause the cells to scatter laser light, and to fluoresce when excited by laser light having the desired wavelength. The portion of the fluorescent light radiating towards dichroic mirror 130 is reflected by dichroic mirror 130 toward dichroic mirror 132. The dichroic mirror 132 in this example will permit the laser-excited fluorescent light, scattered light, or both, to pass to filter 136, which will permit the light to pass to detector 134. The detector 134 provides an electrical signal representative of the detected light to controller 118, which can then analyze the signal to evaluate characteristics of the detected cell, such as cell size, density and granularity.

When the controller 118 is controlling laser 122 to operate in a CW mode, the controller 118 can also control the LED assembly 124 to operate in a CW mode, or preferably, in a pulsed mode. If the controller 118 controls the LED assembly 124 to operate in a continuous mode, the controller 118 provides the appropriate signal to drive circuit 142 (see, for example, FIG. 2), to drive LED 125 in a continuous manner. Light emitted from the LED 125 of LED assembly 124 is focused by lens 126 to pass through optional filter 128 and dichroic mirror 130, and is focused by lens arrangement 111 as a spot (e.g., a 300 $\mu$m×300 $\mu$m spot) onto the sample stream 110. It is noted that the LED spot focused onto the sample stream need not be an in-focus image of the LED emitting surface. Other modes of illumination such as Kohler illumination may be advantageous in certain applications. Kohler provides more uniform but less intense spot of illumination.

As stated above, the LED light excites the stained cells and causes them to fluoresce. The portion of the fluorescent light radiating towards dichroic mirror 130 is reflected by dichroic mirror 130 toward dichroic mirror 132. The dichroic mirror 132 in this example will reflect the LED-excited fluorescent light toward filter 140, which will permit the light to pass to detector 138. This optical configuration where the same lens is used to illuminate and collect light from the sample is known in microscopy as epi-illumination. The detector 138 provides an electrical signal representative of the detected light to controller 118, which can then analyze the signal to evaluate characteristics of the detected cell, such as DNA content or binding of specific fluorescently tagged antibodies.

In the operation described above, the detectors 134 and 138 remain in an "on" conduction. However, the detectors 134 and 138 can be of the type which can be controlled by the controller 118 to operate in an on and off manner at the appropriate detection times.

If the controller 118 controls the LED assembly 124 to operate in a pulsed mode, the controller 118 will provide the appropriate pulsing signal to drive circuit 142 to thus drive the LED 125 in an off and on manner. As can be appreciated by one skilled in the art, unlike arc lamps and gas lasers typically used as light sources in flow cytometry, LEDs can be easily turned on and off on time scales as low as 1 $\mu$s or less. Thus, a cell evaluation assembly 120 employing a laser or other CW light source can be configured so that particles first pass through the CW beam and are detected by the appropriate detector (e.g., detector 134). When the signal provided by detector 134 indicates to the controller 118 that a cell or particle of interest has been detected, the controller 118 can provide a trigger pulse to the drive circuit 142, which pulses the LED 125 on for a predetermined amount of time after the cell has passed through the CW beam. It is noted that as discussed above, the light emitted by laser 124 radiates onto flow stream 110 at a point which is about 100 microns upstream of the point at which the light emitted by LED 125 radiates onto flow stream 110. Therefore, the controller 118 provides the trigger pulse to the drive circuit 142 to turn the LED 125 during the time at which the controller 118 anticipates that the cell of interest will be in the path of the LED light.

Taking measurements by pulsing the LED assembly 124 has several advantages. For example, compared to constant current CW operation, higher currents and higher light output can be used if the duty cycle of the pulses is kept below about 10%, that is, if the LED assembly 124 is off about 90% of the time and on about 10% of the time. Pulsing the LED assembly 124 also eliminates or at least minimizes interference of its light with other measurements made at other times with different light sources. For example, if a UV LED is used to excite DAPI fluorescence, the green component of the DAPI emission could interfere with measuring immunofluorescence with FITC excited with a second, spatially separated blue laser beam. This problem can therefore be eliminated by synchronizing the detectors so that detection of the fluorescence due to excitation of the cells with the blue laser beam occurs when the UV LED is off.

The techniques described above using one or more CW sources, such as a laser operating in a CW mode, in conjunction with one or more LEDs operating in either a CW mode or pulsed mode, are effective in exciting cells or particles of interest in a flow stream for detection and analysis. However, additional techniques can be employed in the flow cytometer 100 to further improve cell detection.

For example, if a cell evaluation apparatus 120 employing one or more LED assemblies is used for DNA analysis, it is desirable to be capable of operating the LED or LEDs to achieve the equivalent of a short (e.g., less than 25 $\mu$m high) excitation beam to enable the system to perform doublet (size) discrimination of the cells, while also achieving the equivalent of a tall excitation beam to take advantage of the large LED excitation spot and to provide as much excitation light as possible to obtain the best signal to noise ratio. These capabilities can be achieved using a double slit approach as will now be described.

Figure 8:
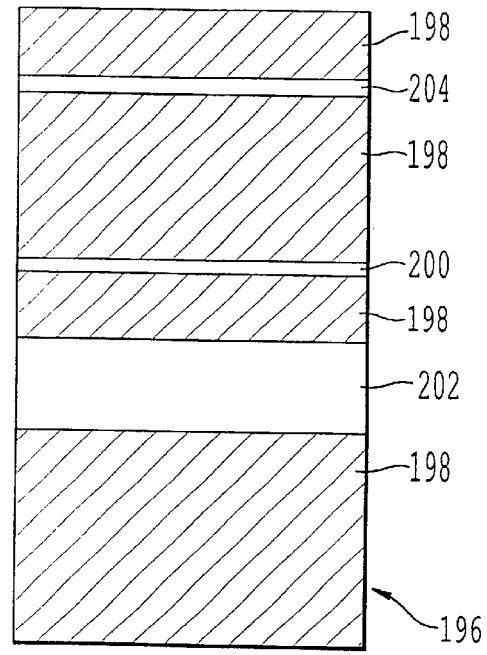
FIG. 8 is an example of a panel having slits for use with the apparatus shown in FIGS. 1–3.

Specifically, an aperture assembly or panel 196 as shown in FIG. 8 can be used in conjunction with detectors 134 and 138 to achieve the effect of short and tall excitation beams as described above. A panel 196 can be placed on, in front of, or behind the filter of each detector that is to be used to detect LED light. The panel 196 can also be made integral with the filter. For example, in the cell evaluation assembly 120 described above, detector 138 is used to detect LED light: Therefore, panel 196 is employed with filter 140. Regardless of where the panel 196 is placed with respect to the filters and respective detectors, the panel 196 should be in the image plane of lens 111, which is the plane at which the lens 111 focuses the image of the sample stream 109.

As illustrated, panel 196 has opaque regions 198 which are impermeable or essentially impermeable to light, and slit regions 200 and 202. As shown, slit region 200 is narrower than slit region 202. In this example, slit region 200 has a height of about 0.4 mm, while slit region 202 has a height of about 2.0 mm. However, the height of slit regions 200 and 202 can be any suitable size. In addition, panel 196 includes an area 204 representative of the location at which the laser beam emitted from laser 122 strikes the sample stream 110 in relation to the location (i.e., the area encompassing slit regions 200 and 202) at which the light emitted from the LED strikes the sample stream 110. In this example, area 204 is blocked because the fluorescent light emitted from the cells due to excitation by the laser beam is not directed to filter 140, but rather, is directed to filter 136 associated with detector 134 (see FIGS. 1–3).

Figure 9:
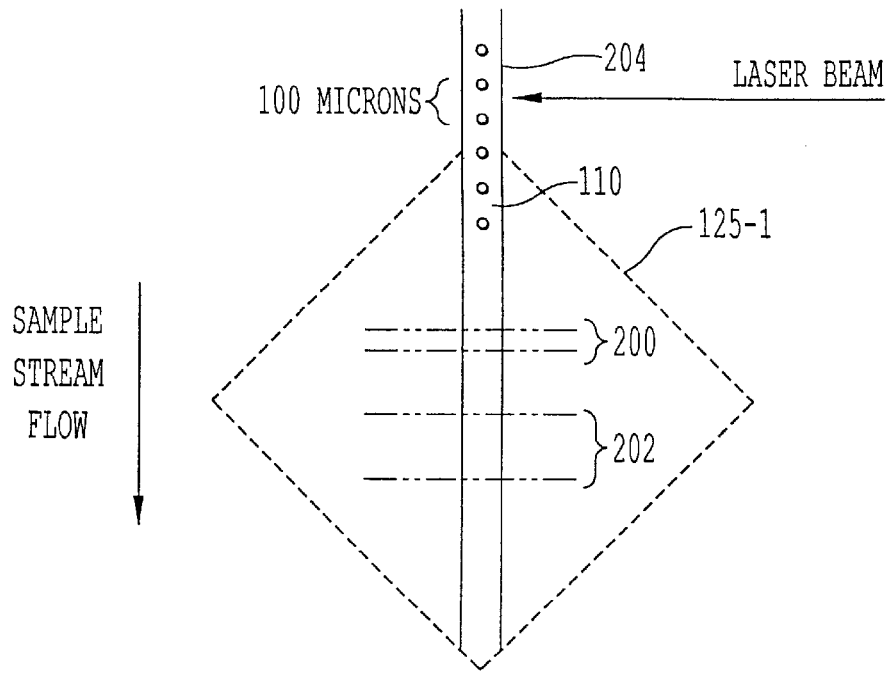
FIG. 9 is a conceptual illustration of the LED-generated excitation light being emitted on the sample stream in relation to the positions of the slits in the panel shown in FIG. 8 in accordance with an embodiment of the present invention.

FIG. 9 is a conceptual diagram illustrating the location of the slit regions 200 and 202 relative to the area of the sample stream 110 illuminated by the LED light. As discussed above, an LED 125 employed in an LED assembly 124 can be a Nichia LED having an emission surface of about 0.3 mm×0.3 mm square. The condenser lens 126 and the lens arrangement 111 focus the image 125-1 of light emitting surface of the LED 125 onto the sample stream 110 as shown by dotted lines in FIG. 9. The sample stream 110 is flowing in a downward direction as shown. The lens arrangement 111 images the sample stream 110 onto the aperture assembly or panel 196 via the arrangement of the dichroic mirrors 130 and 132 as described above with reference to FIGS. 1–3. However, as further shown in FIG. 9, the panel 196 only permits the portions of the image corresponding to the locations of the slit regions 200 and 202 (represented by dashed-dotted lines) to pass to the detector 138. Therefore, as will now be described, the controller 118 can control the detector 138 to detect light at intervals when a cell of interest is present in the cell stream 110 at a location corresponding to the image that passes through slit region 200, and when the cell of interest is present in the cell stream 110 at a location corresponding to the image that passes through slit region 202.

In the above arrangement, the panel 196 is located to block light entering a detector, such as detector 138, so that only light that passes through the short and tall slits is detected. However, a panel 196 can also be located on the excitation side or, in other words, in the path of the excitation light propagating from the LED, to create narrow and long spots of LED excitation along the sample stream 110.

Figure 10:
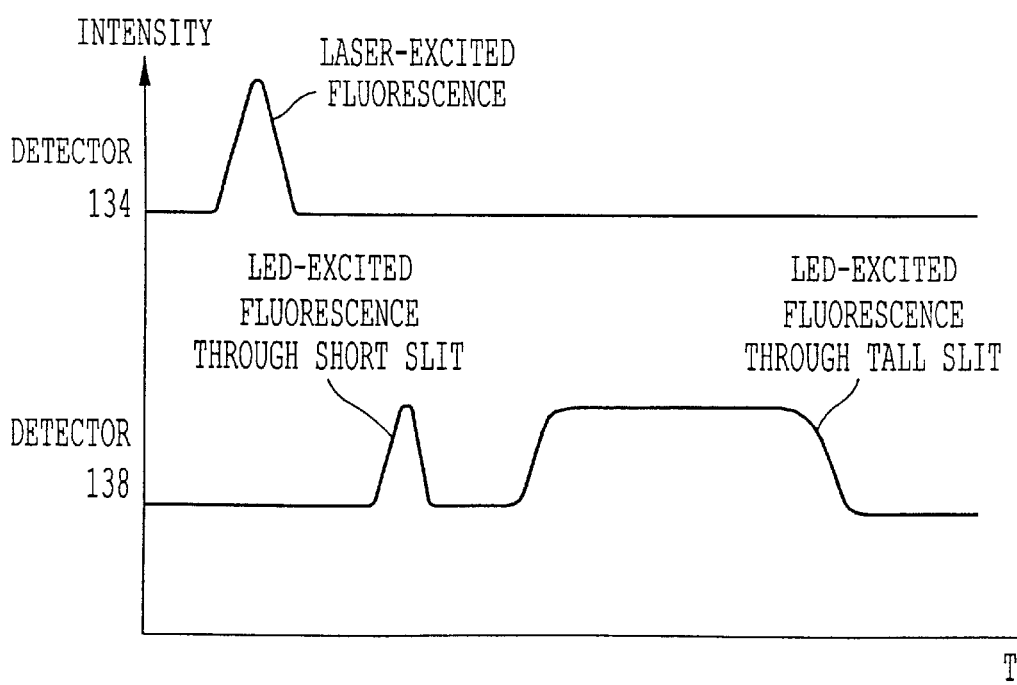
FIG. 10 is an example of a timing diagram illustrating detection of laser-excited fluorescence in relation to LED-excited fluorescence in an apparatus employing the panel shown in FIG. 8.

FIG. 10 is a timing diagram illustrating the relationship between the time at which detector 134 detects the laser-excited fluorescence with respect to the times at which detector 138 detects the LED-excited fluorescence through slit regions 200 and 202. That is, because a stained cell in flowing sample stream 110 will first pass through and being excited by the laser beam, the detector 134 will detect the laser-exited fluorescence first, as indicated by the narrow pulse for the detector 134 waveform in FIG. 10. The stained cell then moves into the LED light illuminated region of the sample stream 110. When the stained cell is at a location in the sample stream 110 that corresponds with slit region 200, the LED-excited fluorescence emitted from the cell will pass through slit region 200 and be detected by detector 138, as indicated by the narrow "size or doublet discrimination" pulse in the waveform for detector 138 in FIG. 10. As the stained cell then passes into a region in the sample stream 110 that corresponds with slit region 202, the LED-excited fluorescence emitted from the cell will pass through slit region 202 and be detected by detector 138, as indicated by the wide "measuring" pulse in the waveform for detector 138 in FIG. 10. Typically, the detected LED-excited fluorescence that has passed through short slit region 200 is used by the controller 118 to perform doublet discrimination or, in other words, to evaluate the size of the cell. The detected LED-excited fluorescence that has passed through tall slit region 202 is used by the controller 118 to evaluate other characteristics of the cell, such as DNA content.

As discussed above, the detected laser-excited fluorescence can be used by controller 118 to control pulsing of the LED 125 of LED assembly 124. That is, since the velocity of the sample stream 110 is known, the controller 118 can provide the appropriate pulse to drive circuit 142 at the appropriate time after the laser-excited fluorescence is detected by detector 134, so that the LED 125 is turned on only at the time that a stained cell of interest is present in the LED illumination region of flow stream 110. This LED pulsing has the advantages discussed above, such as decreasing power usage, extending the life of the LED, and preventing interference by the LED light with excitation light from other sources.

Instead of using the detected laser-excited fluorescence to control pulsing of the LED 125, the controller 118 can base the pulsing of the LED 125 based on the LED-excited fluorescence detected through short slit region 200. An example of this technique will now be explained with reference to the timing diagram shown in FIG.

Figure 11:
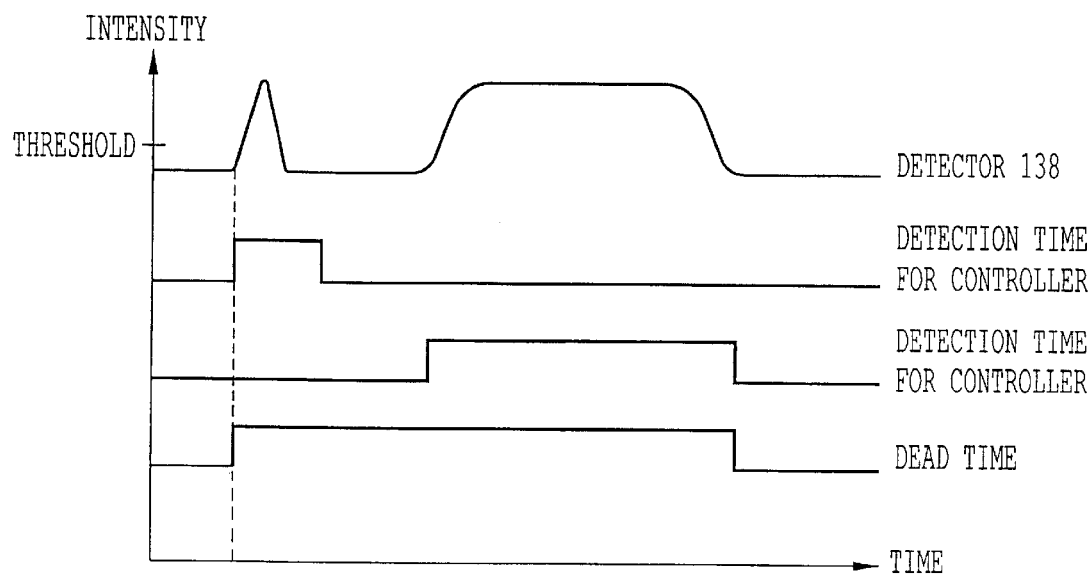
FIG. 11 is an example of a timing diagram in which pulsing of the excitation LEDs is based on detection of LED-excited fluorescence through a small slit in the panel shown in FIG. 8 in accordance with an embodiment of the present invention.

The uppermost waveform in FIG. 11 is similar to the lower waveform in FIG. 10 in that it represents the detection of LED-excited fluorescence by detector 138 through the short slit region 200 and tall slit region 202, as indicated by the narrow and wide pulses, respectively. The second and third waveforms represent the periods of time, as indicated by the pulses, during which the controller 118 receives the signal representative of the detections, from detector 138. The fourth waveform represents the period of "dead time", meaning the total time during which the controller 118 is detecting signals from the detector 138. It is noted that the pulses shown in the second and fourth waveforms each begin when the first detection intensity pulse provided by detector 138 reaches a predetermined threshold.

Figure 12:
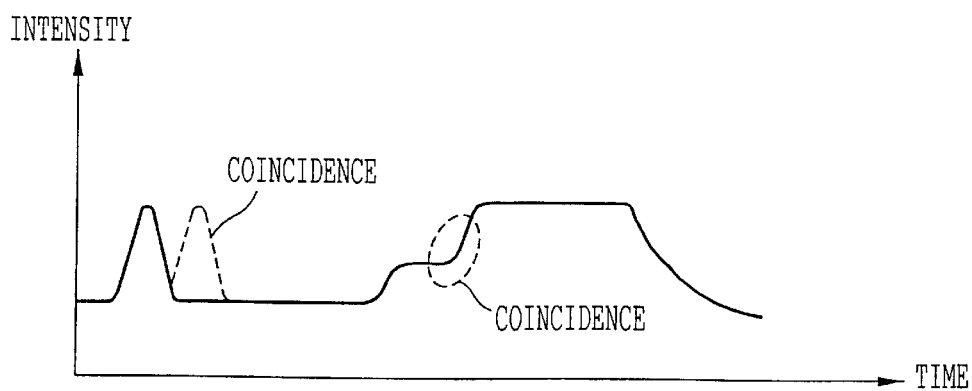
FIG. 12 is a timing diagram illustrating the presence of a coincidence in a LED-excited fluorescence pulse detected through a large slit in the panel shown in FIG. 8.

During the dead time shown in FIG. 11, the controller 118 can detect whether a coincidence (i.e., the presence of another cell) has been detected by detector 138 during the time that the detector 138 is detecting light from a cell. It is noted that if controller 118 senses that an inflection indicative of coincidence has occurred in the intensity of the LED-excited fluorescence as detected by detector 138 through short slit region 200 or tall slit region 202, as shown in FIG. 12, then the measurement of that cell is aborted.

Experimental Results

The following is a discussion of specific results that have been obtained using the techniques described above.

EXAMPLE 1

Figure 13:
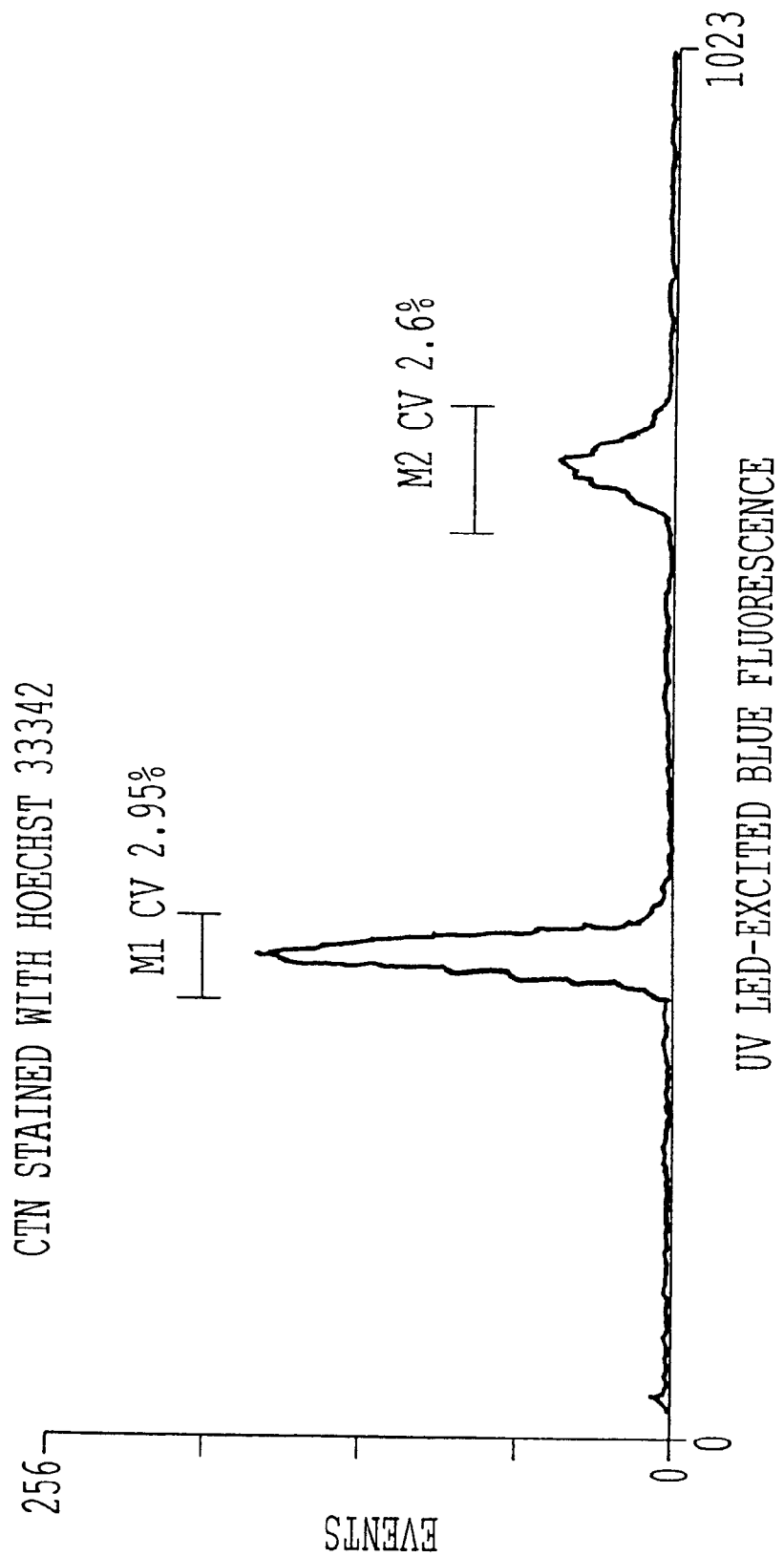
FIG. 13 is a graphical representation of events detected by a flow cytometer employing an ultraviolet (UV) LED as an excitation light source.

A UV LED was incorporated into a modified FACScan in an epi-illumination configuration. A condenser lens collected light from the LED, focused it to where the slit associated with a PMT detector designated as FL1 is normally located, and the FACScan condenser lens re-focused this image onto the sample stream. The image of the LED chip on the sample stream is much larger than the focused laser spot used in a FACScan, so fluorescence pulses were about 25 μs long rather than 3–5 μs as is typical for laser excitation. UV-excited fluorescence was collected through a 420 nm high pass filter. Calf thymocyte nuclei (CTN) from the DNA QC kit were stained with Hoechst 33342 (10 μg/ml), and analyzed on the UV breadboard. CV's between 3–4% were obtained in several runs under slightly different conditions. The fluorescence histogram obtained with the best configuration is shown in FIG. 13.

It is noted that the results discussed above will improve as the intensity of the LEDs are improved. For example, if the intensity of the 370 nm, 470 nm and 520 nm LEDs is increased to within the range of 5 mW to 5.5 mW output, a doubling of current power and 5-fold increase in the signal detection for the UV, green and blue-green LEDs. Also, pulsing the LED allows higher currents to be used and increases the UV output by about 2.5 times.

It is further noted that the UV LED could be incorporated into a FACScan or FACSCalibur manufactured by Becton-Dickinson and Company for single-color UV excited fluorescence, with minor modification to existing electronics in these instruments. The UV-excited fluorescence would be an additional parameter to existing fluorescence parameters. A UV LED could also be added to a FACSCount manufactured by Becton Dickinson and Company to allow industrial applications requiring UV excitation.

In addition, very small, low cost flow cytometers are possible if LEDs are used for light sources. For many applications, a moderate power (5 mW) 635 nm diode laser could provide good immunofluorescence, and UV, blue and green LEDs could provide excitation for brightly fluorescing stains or for immunofluorescence on cells with high amount of antigen (e.g. cryptosoridium). The use of LEDs also provide a very low cost option for UV-excited DNA analysis. The LED technology described above can also be used with other brightly staining UV dyes for detection of bacteria, yeast, and biochemical components such as protein, glutathione, and DNA using DAPI or other UV excited fluorochromes for nucleic acids.

EXAMPLE 2

Figure 14A:
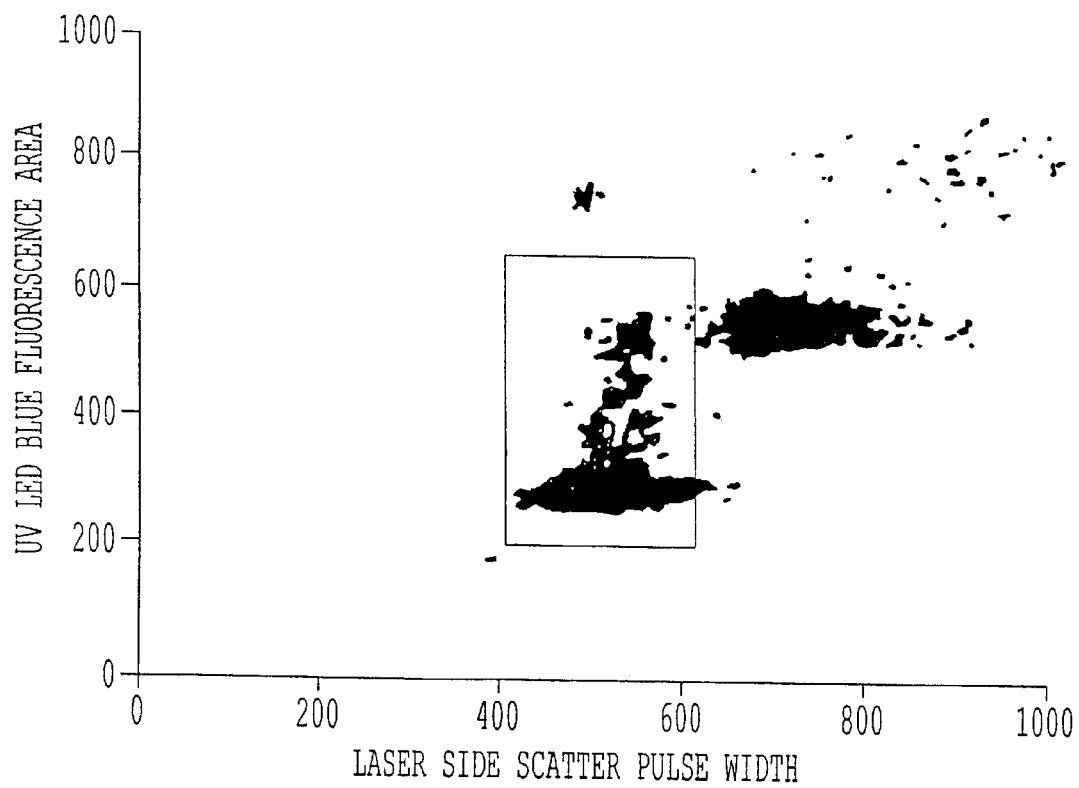
FIG. 14A is a scatter plot diagram illustrating exemplary results obtained in a system according to an embodiment of the present invention employing a UV LED and 635 nm diode laser.
Figure 14B:
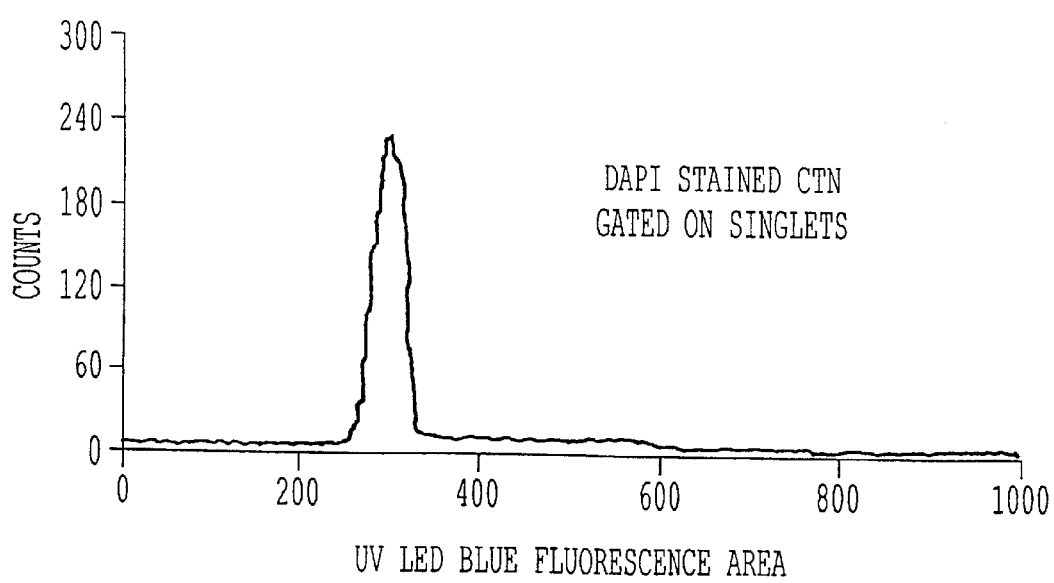
FIG. 14B is a histogram representation of the data shown in FIG. 14A.

A UV LED was employed as LED 125 in an arrangement according to the embodiments described above. FIG. 14A is an exemplary scatter plot of UV LED excitation of DAPI stained calf thymoycte nuclei (CTN). UV-excited blue fluorescence pulse area measured DNA content and doublet discrimination used laser side scatter pulse width. FIG. 14B is an exemplary histogram of the results shown in FIG. 14A.

EXAMPLE 3

Figure 15A:
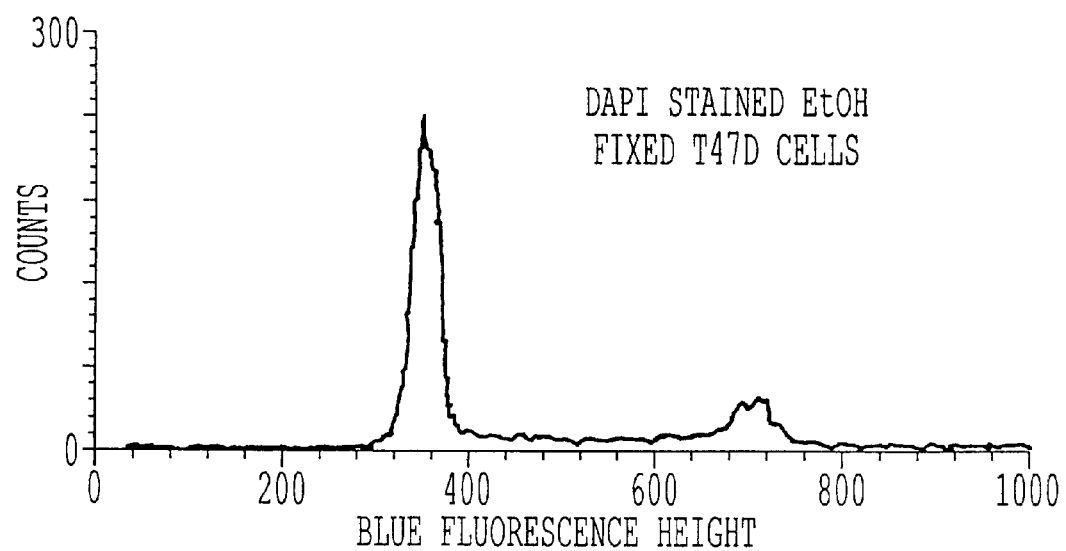
FIGS. 15A and 15B are histograms illustrating exemplary results obtained in a system according to an embodiment of the present invention employing a UV LED.
Figure 15B:
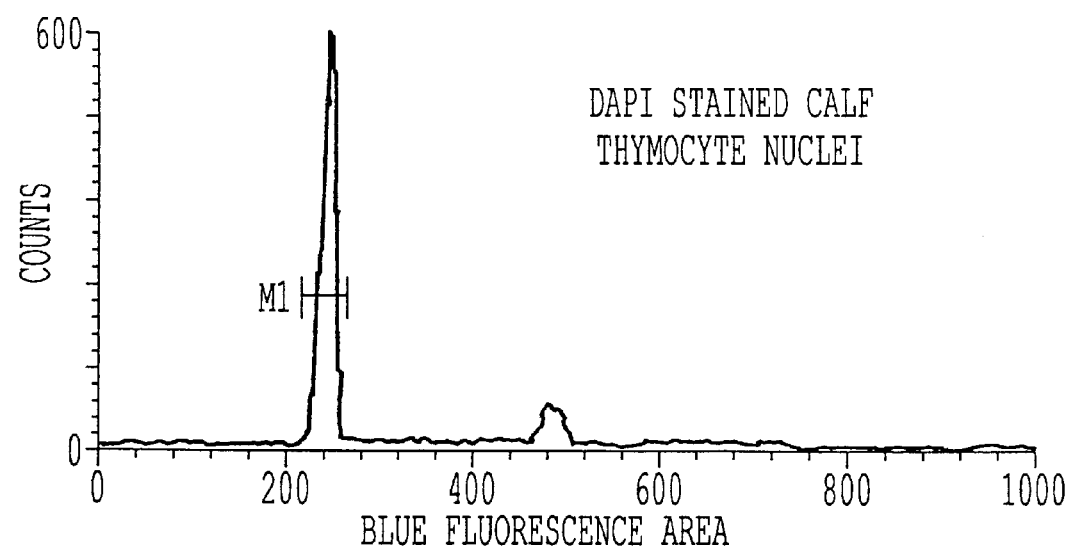

A UV LED was employed as LED 125 in an arrangement according to the embodiments described above. FIGS. 15A and 15B are exemplary DNA histograms of results obtained for formaldehyde-fixed calf Thymocyte nuclei (CTN, upper panel) and ethanol-fixed T47D cells stained with DAPI. The CV of the G0/G1 peak of the CTN is 2.0%.

EXAMPLE 4

Figure 16A:
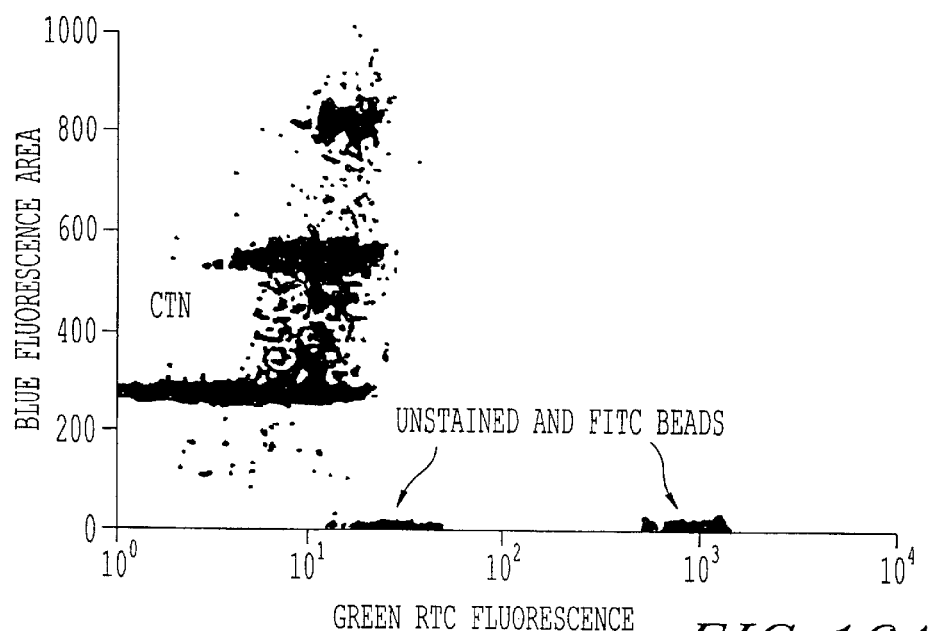
FIG. 16A is a scatter plot diagram illustrating exemplary results obtained in a system according to an embodiment of the present invention employing a UV LED and a 488 nm laser.
Figure 16B:
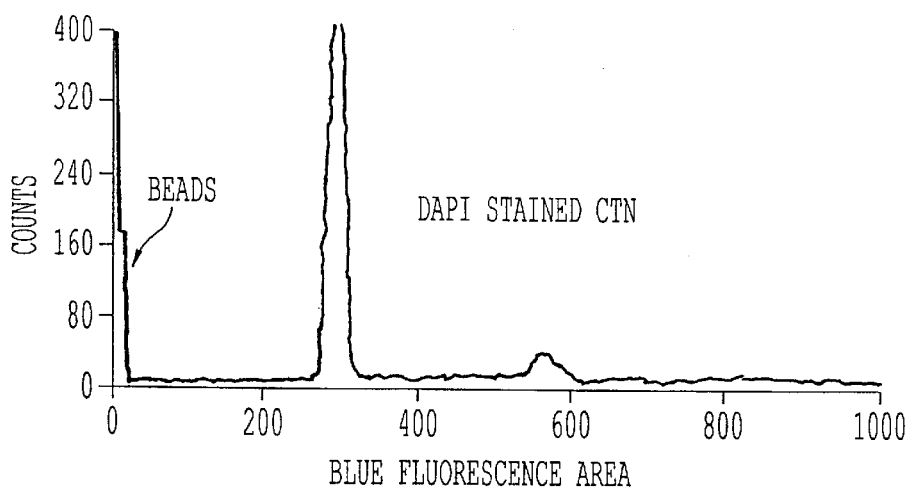
FIGS. 16B and 16C are histogram representations of the data shown in FIG. 16A.
Figure 16C:
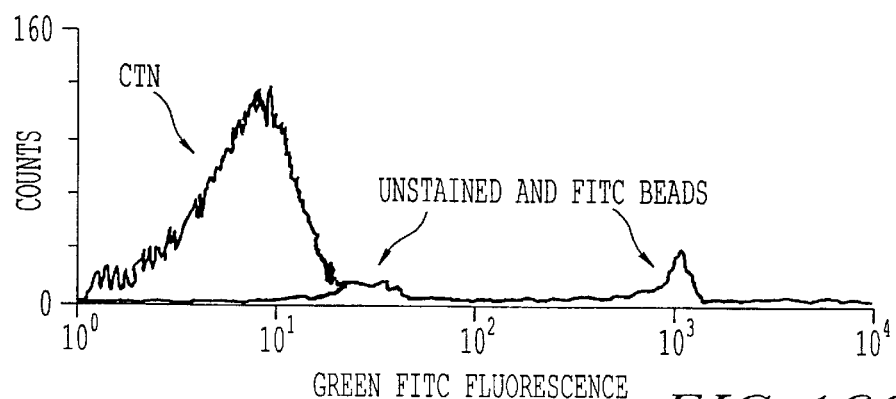

A UV LED was employed as LED 125, and a 488 nm laser was employed as laser 122 in an arrangement according to the embodiments described above. The scatter plot of FIG. 16A and the histograms of FIGS. 16B and 16C illustrate exemplary results obtained for UV LED excited DNA and 488 nm laser excited fluorescein isothiocyanate (FITC) fluorescence. The sample was a mixture of unstained and FITC CaiBRITE beads and calf thymocyte nuclei (CTN), a staining solution containing 1 microgram/ml of DAPI. The filter stack for blue DAPI fluorescence included a 488 nm band reject filter.

EXAMPLE 5

Figure 17:
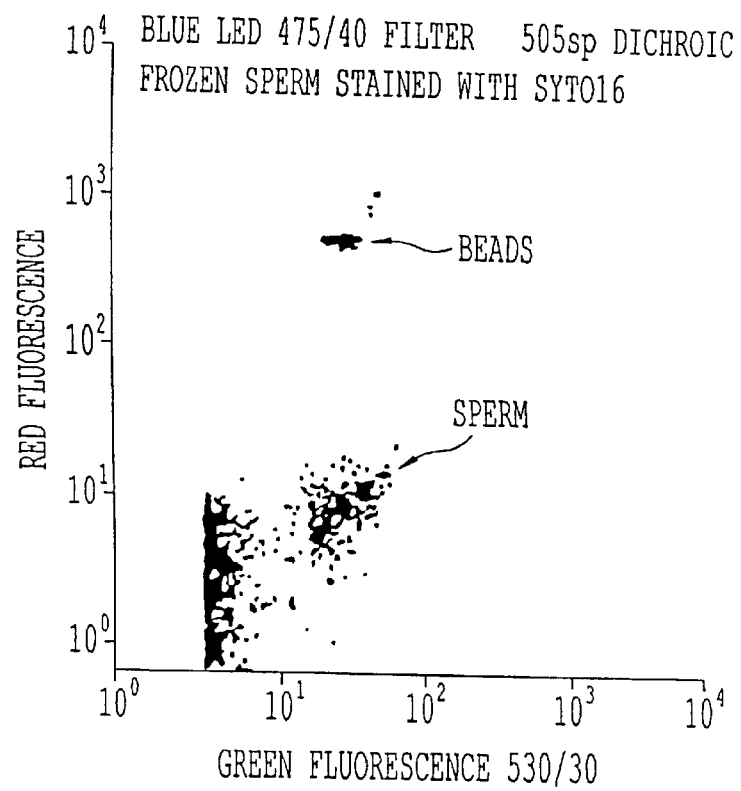
FIG. 17 is a scatter plot diagram illustrating exemplary results obtained in a system according to an embodiment of the present invention employing a blue 470 nm LED.

A blue 470 nm LED was employed as LED 125 in an arrangement according to the embodiments described above. FIG. 17 is a scatter plot showing exemplary results obtained for frozen bull sperm stained with Syto16 and analyzed with the blue 470 nm LED. A known number of beads added to the sample allow absolute count of the number of sperm per ml.

EXAMPLE 6

Figure 18:
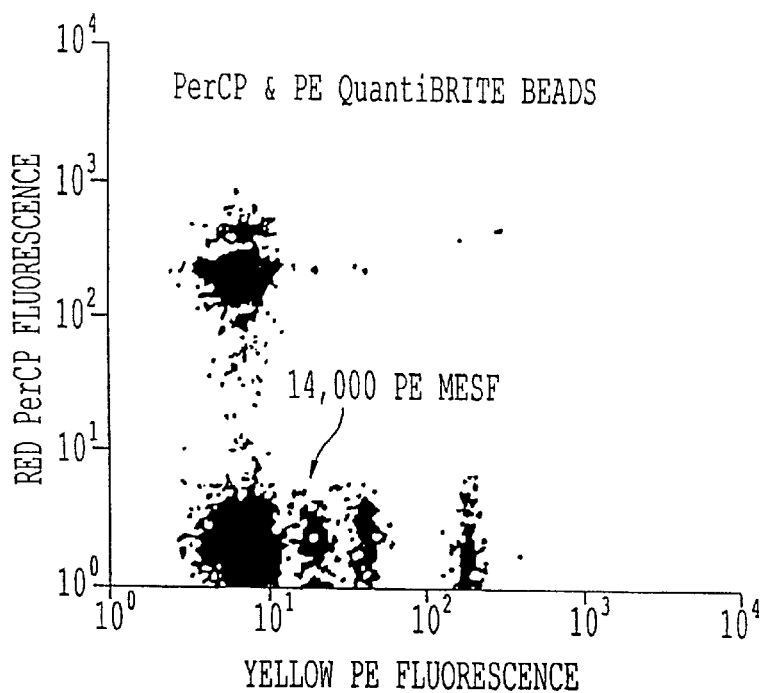
FIG. 18 is a scatter plot diagram illustrating exemplary results obtained in a system according to an embodiment of the present invention employing a blue 470 nm LED that is pulsed.

A blue 470 nm LED was employed as LED 125 in a pulsed manner in an arrangement according to the embodiments described above. FIG. 18 is a scatter plot illustrating exemplary results obtained for a mixture of phycoerythrin (PE) QuantiBRITE Unstained and PerCP CaiBRITE beads excited with a pulsed blue (470 nm) LED. The QuantiBRITE beads area a mixture of 4 different intensity levels (1400, 14000, 38800, and 182000 PE molecules). All PE levels except the 1400 PE molecule level are resolved from unstained beads. Background fluorescence of the unstained beads is 8400 PE molecules.

EXAMPLE 7

Figure 19:
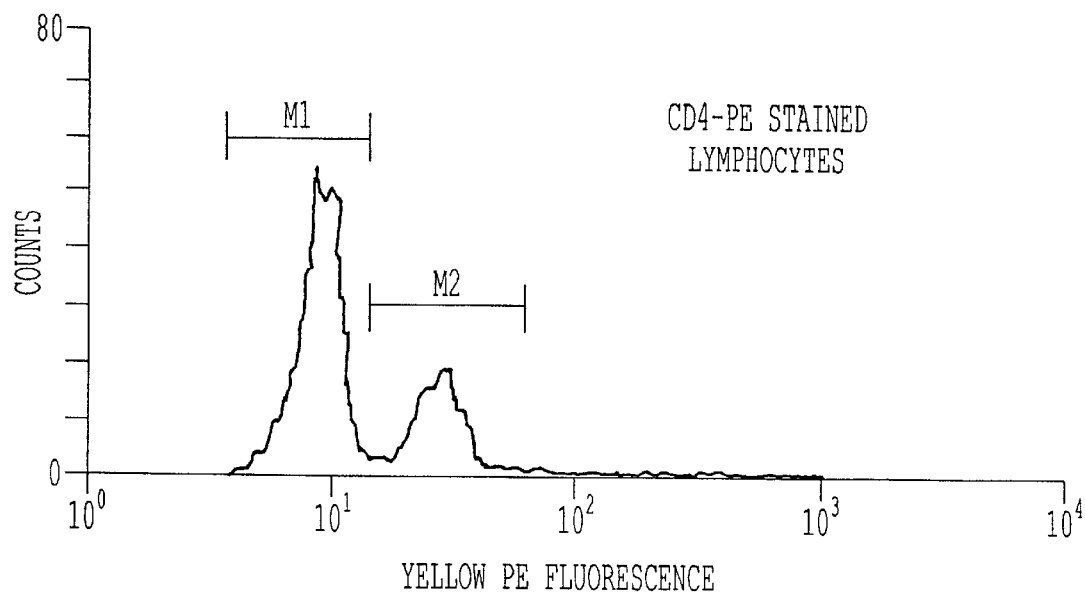
FIG. 19 is a histogram illustrating exemplary results obtained in a system according to an embodiment of the present invention employing a blue 470 nm LED that is pulsed.

A blue 470 nm LED was employed as LED 125 in a pulsed manner in an arrangement according to the embodiments described above. FIG. 19 is a scatter plot illustrating exemplary results obtained for lymphocyte immunofluorescence using CD4-PE with a lyse no-wash sample preparation. The negative peak (M1) has fluorescence equivalent to 7,800 PE molecules. The stained population (M2) has fluorescence equivalent to 24,000 PE molecules. The high level of the negative peak is due primarily to background fluorescence of optical components created when the blue (470 nm) LED is pulsed on. A red diode laser was used as laser 122 described above to measure forward and side scatter to gate fluorescence on the lymphocyte population.

EXAMPLE 8

Figure 20:
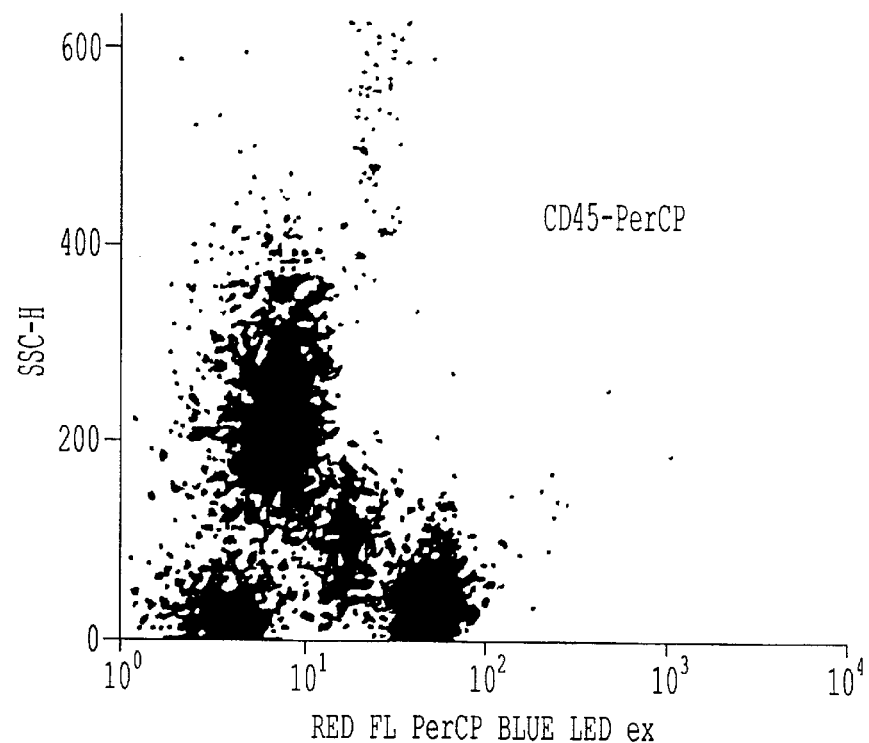
FIG. 20 is a scatter plot diagram illustrating exemplary results obtained in a system according to an embodiment of the present invention employing a blue 470 nm LED that is pulsed.
Figure 21A:
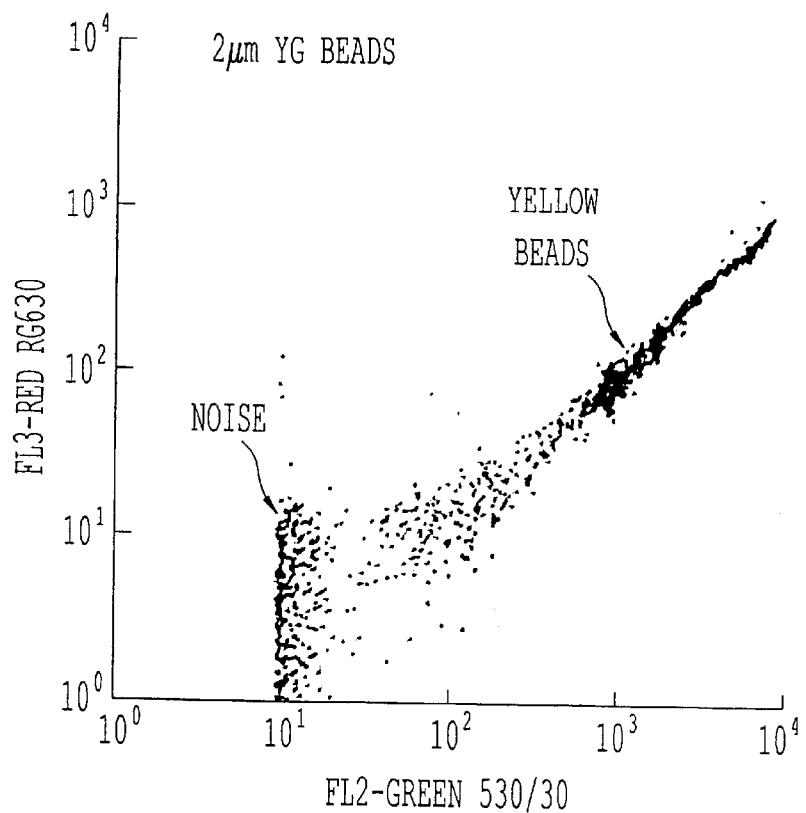
FIG. 21A is a scatter plot diagram illustrating exemplary results obtained in a system according to an embodiment of the present invention employing a Nichia blue LED.
Figure 21B:
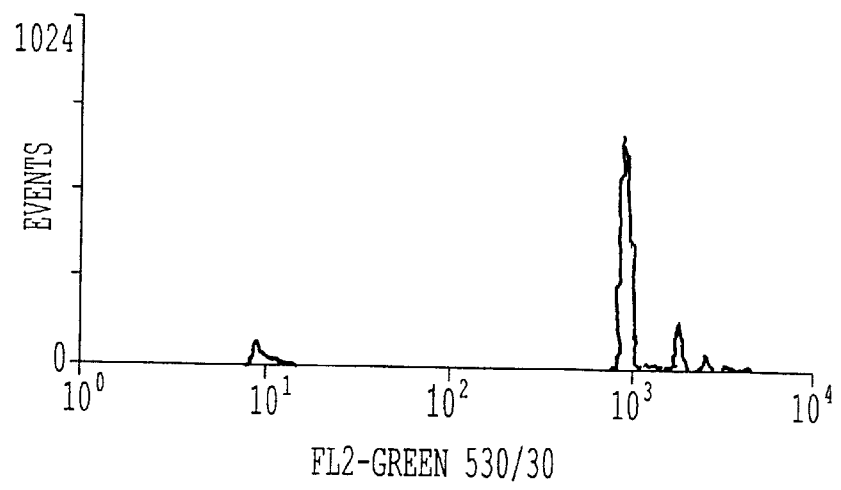
FIG. 21B is a histogram representation of the data shown in FIG. 21A.
Figure 22A:
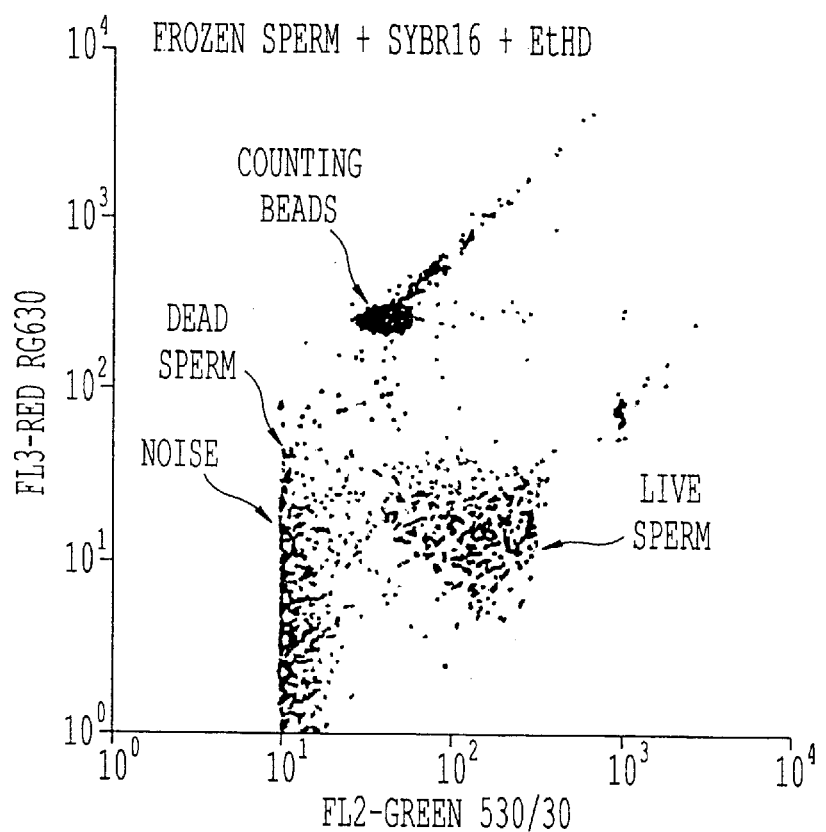
FIG. 22A is another scatter plot diagram illustrating exemplary results obtained in a system according to an embodiment of the present invention employing a Nichia blue LED.
Figure 22B:
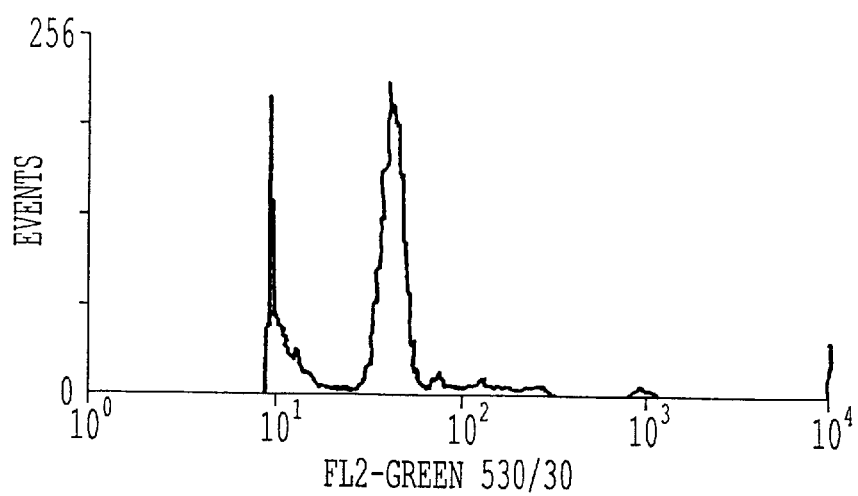
FIG. 22B is a histogram representation of the data shown in FIG. 22A.
Figure 23A:
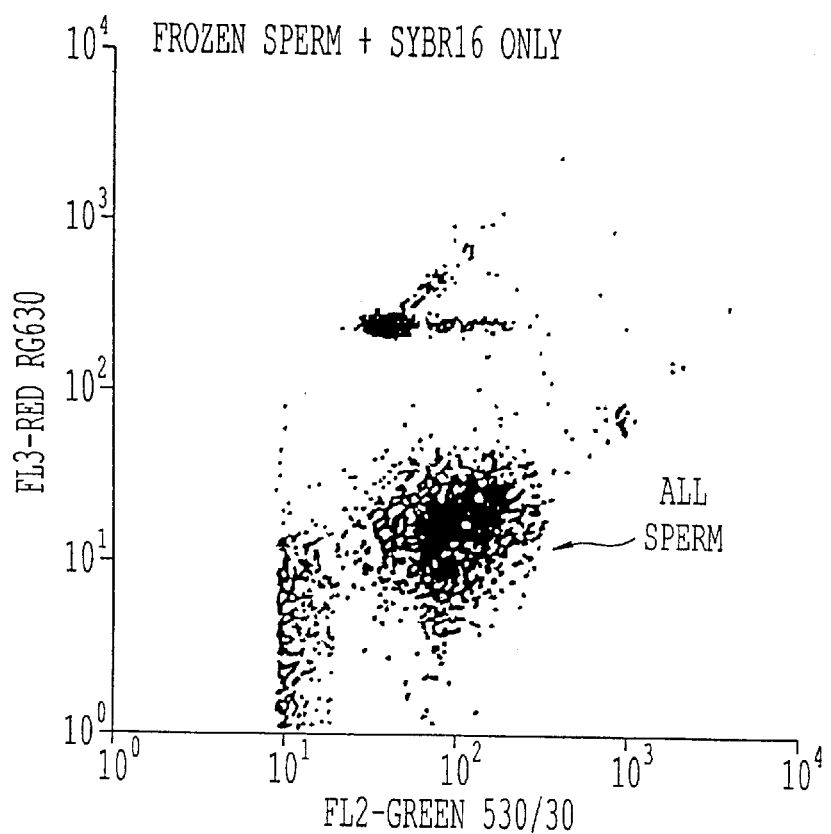
FIG. 23A is a scatter plot diagram illustrating exemplary results obtained in a system according to an embodiment of the present invention employing a blue LED.
Figure 23B:
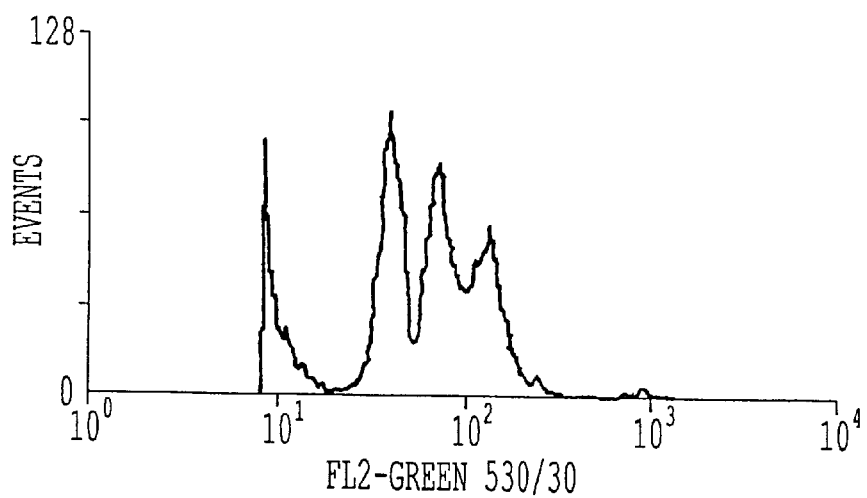
FIG. 23B is a histogram representation of the data shown in FIG. 23A.
Figure 24A:
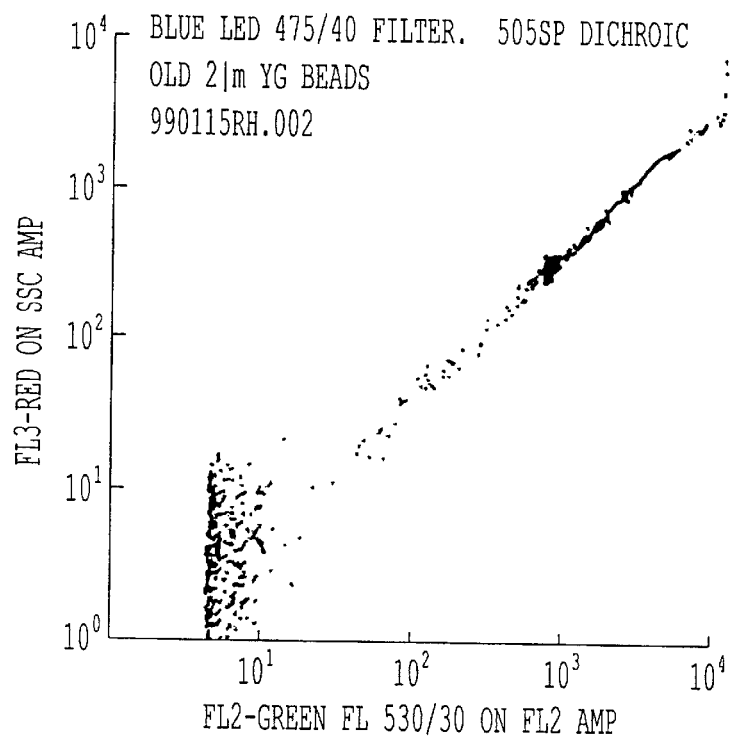
FIGS. 24A and 24B are scatter plot diagrams illustrating exemplary results obtained in a system according to an embodiment of the present invention employing a blue LED.
Figure 24B:
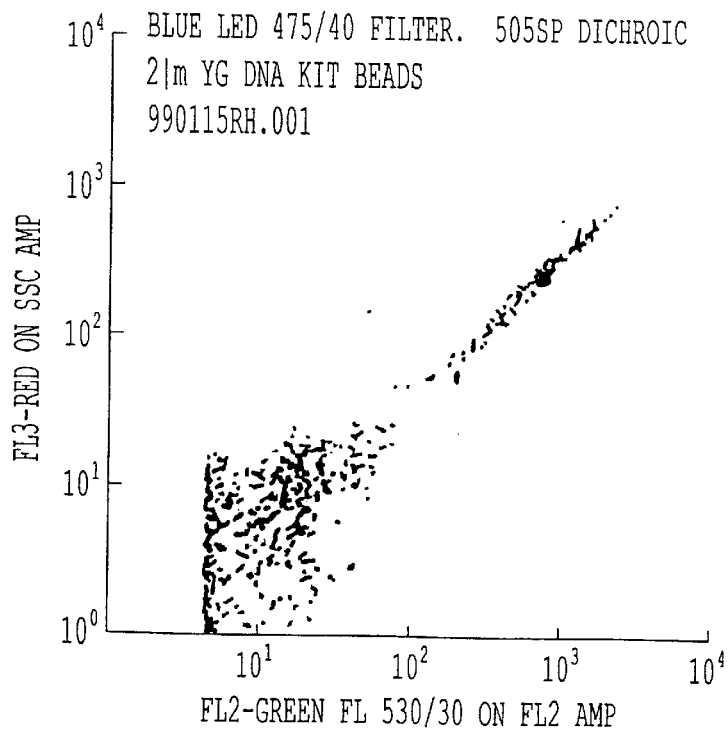
Figure 25A:
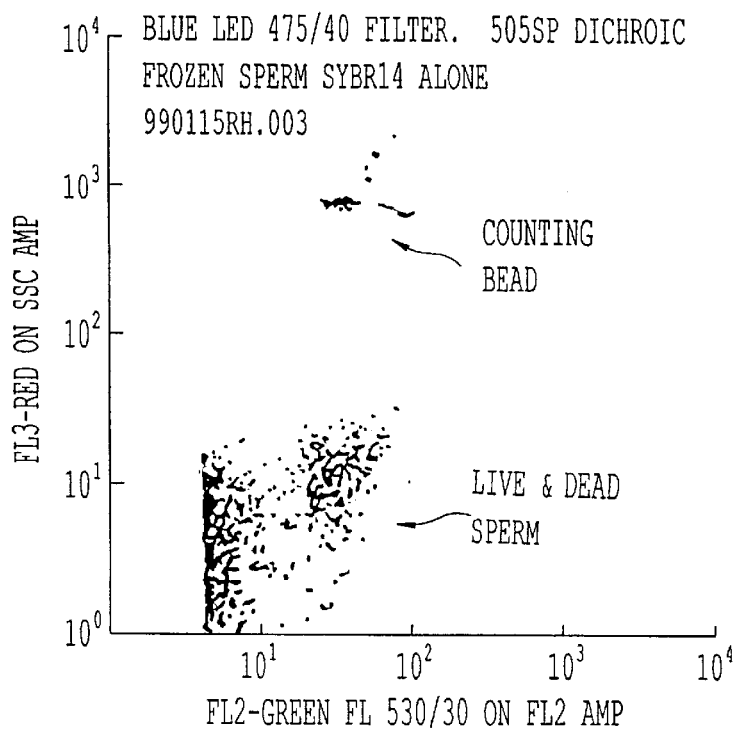
FIGS. 25A and 25B are scatter plot diagrams illustrating exemplary results obtained in a system according to an embodiment of the present invention employing a blue LED.
Figure 25B:
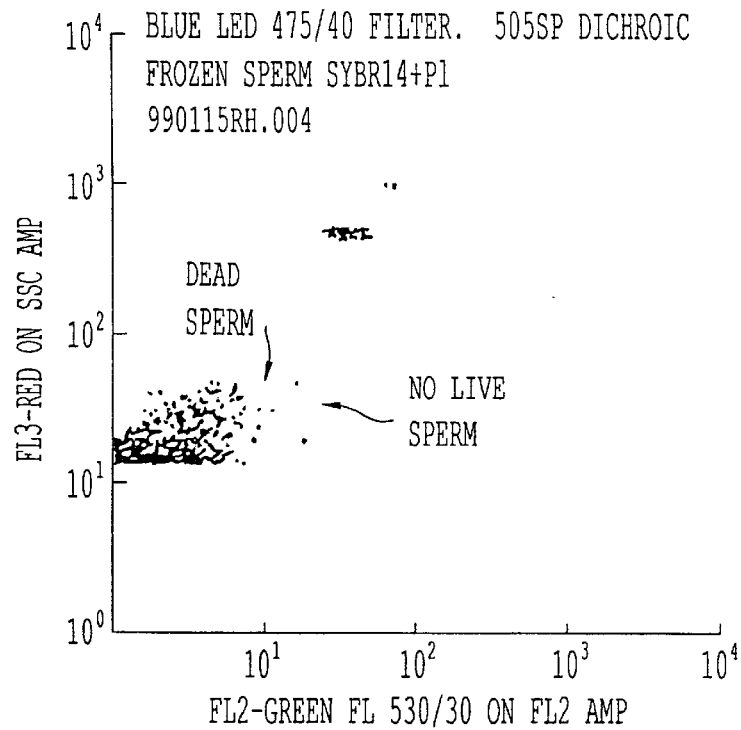
Figure 26A:
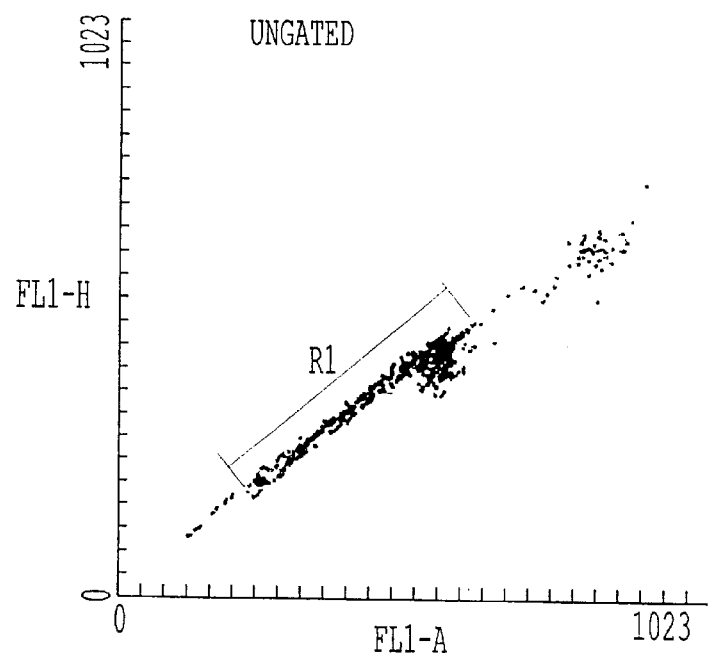
FIGS. 26A and 26B are scatter plot diagrams illustrating exemplary results obtained in a system according to an embodiment of the present invention employing a UV LED.
Figure 26B:
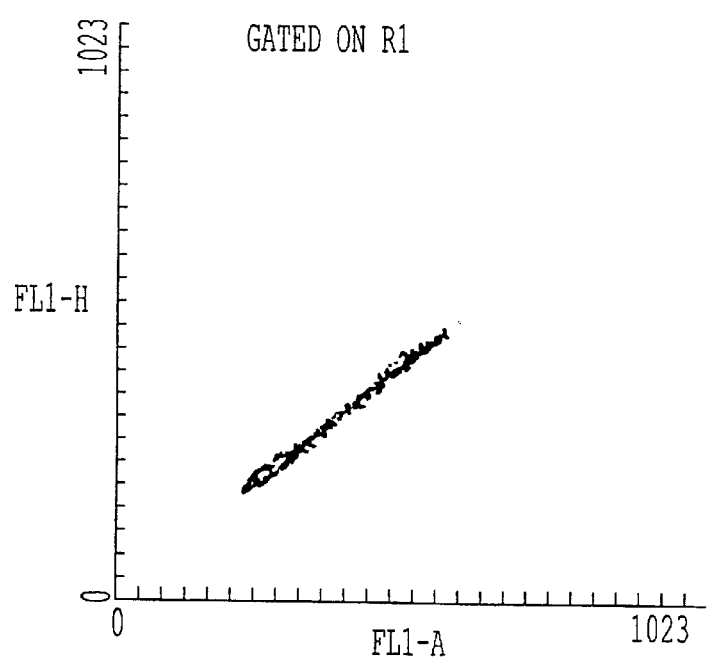
Figure 27A:
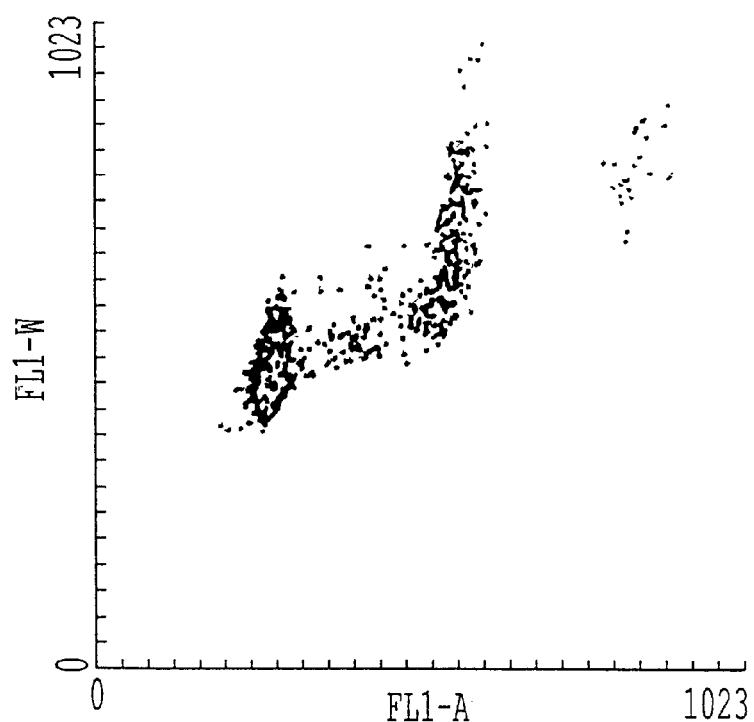
FIG. 27A is a scatter plot diagram illustrating exemplary results obtained in a system according to an embodiment of the present invention employing a UV LED.
Figure 27B:
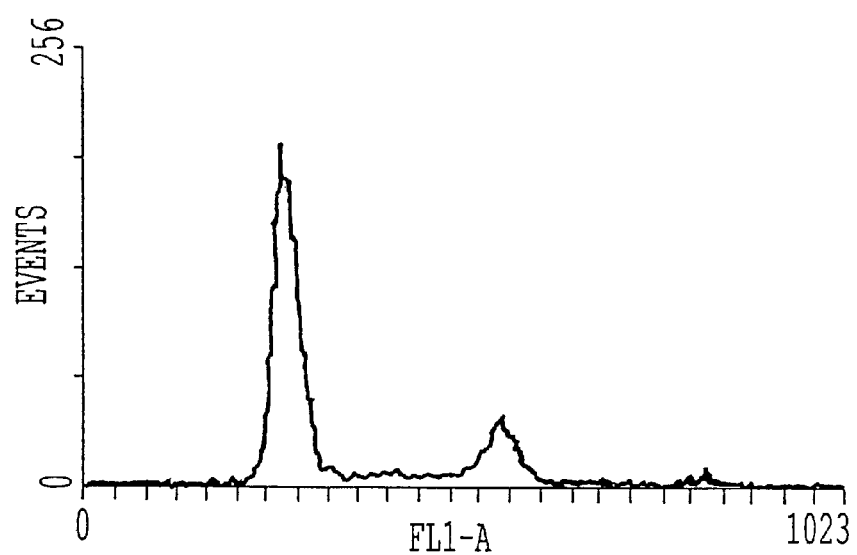
FIG. 27B is a histogram representation of the data shown in FIG. 27A.
Figure 28A:
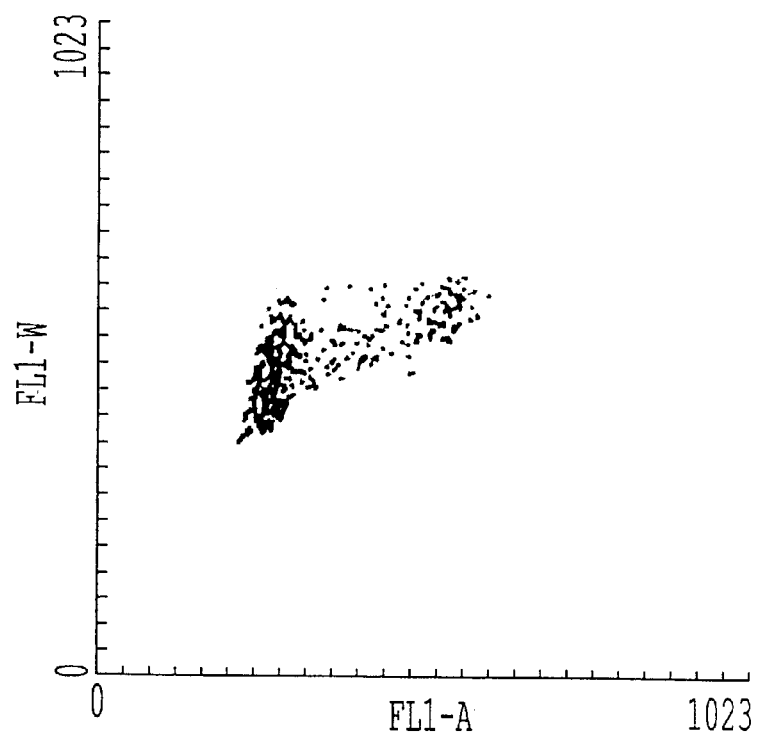
FIG. 28A is a scatter plot diagram illustrating exemplary results obtained in a system according to an embodiment of the present invention employing a UV LED.
Figure 28B:
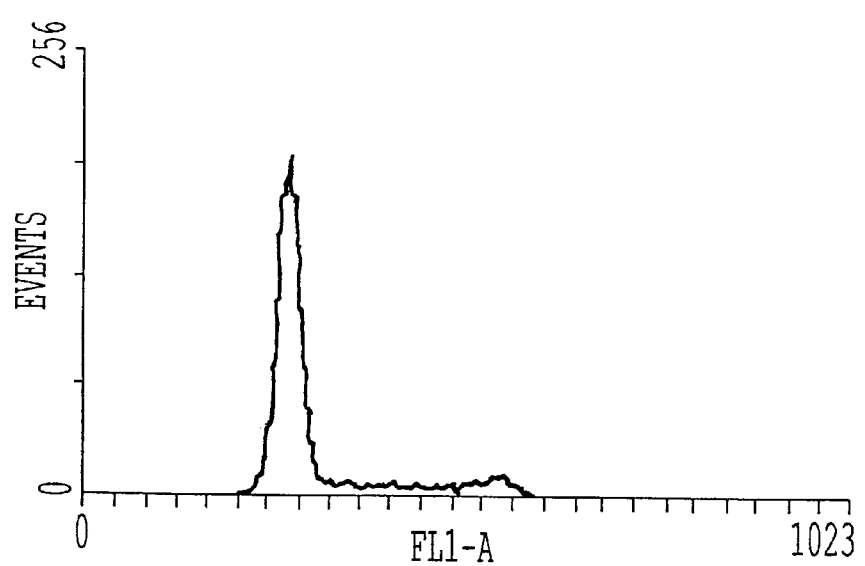
FIG. 28B is a histogram representation of the data shown in FIG. 28A.
Figure 29A:
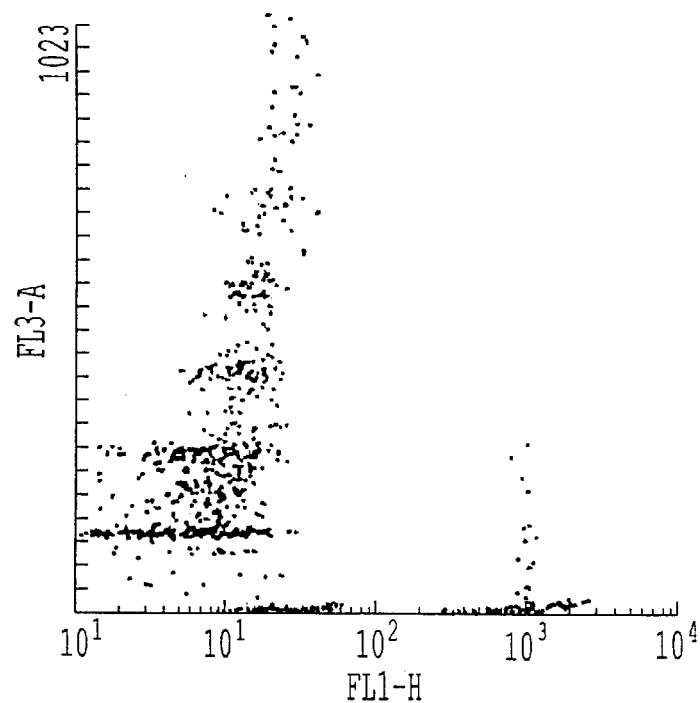
FIGS. 29A and 29B are scatter plot diagrams illustrating exemplary results obtained in a system according to an embodiment of the present invention employing a UV LED.
Figure 29B:
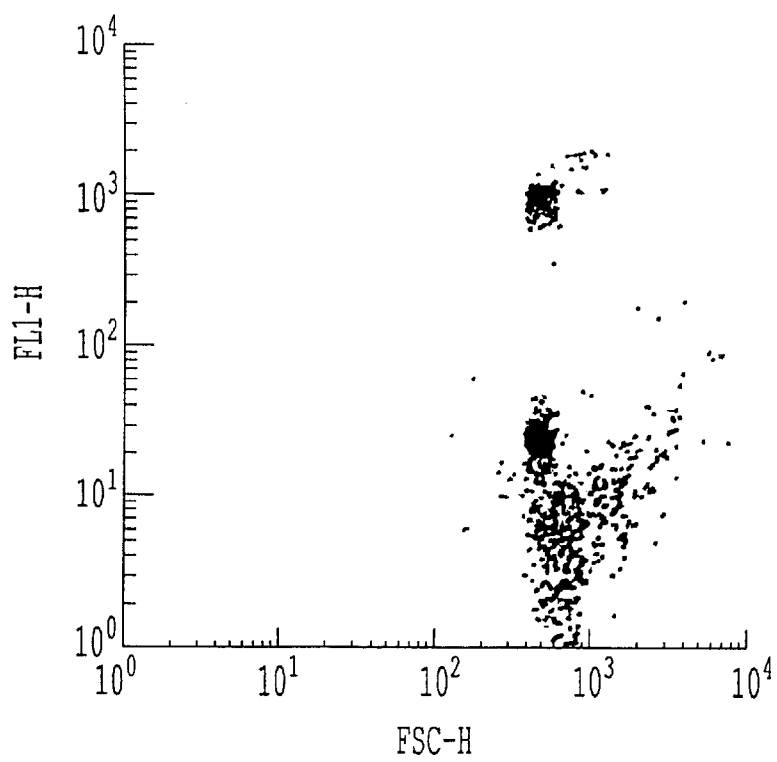
Figure 29C:
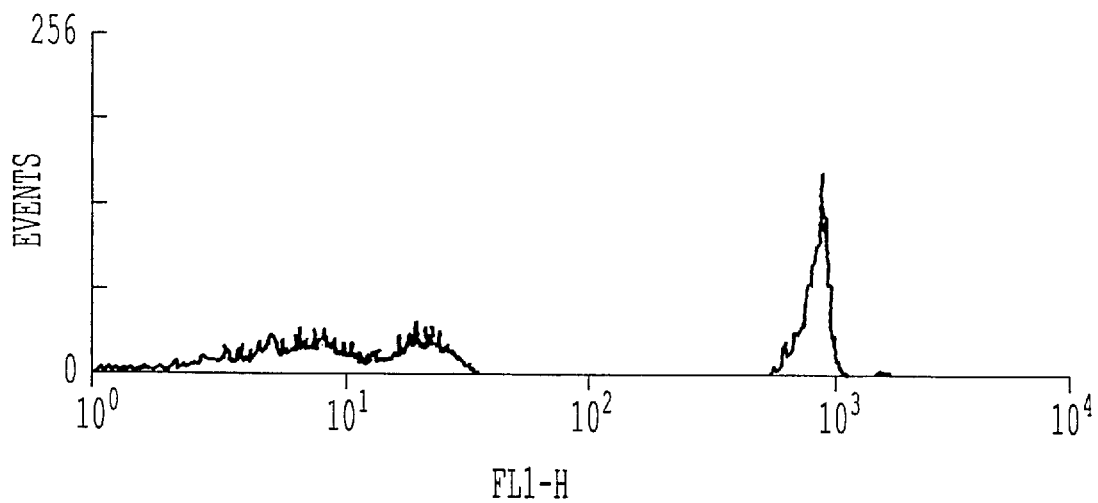
FIGS. 29C and 29D are histogram representations of the data shown in FIGS. 29A and 29B.
Figure 29D:
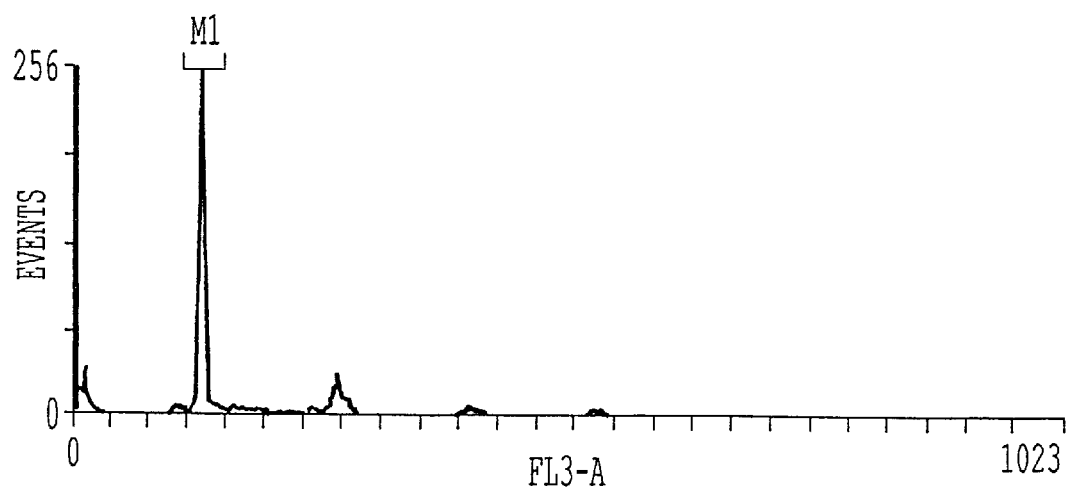

A blue 470 nm LED was employed as LED 125 in a pulsed manner in an arrangement according to the embodiments described above. FIG. 20 is a scatter plot illustrating exemplary results obtained for side scatter vs. CD45 for whole blood stained with CD45-PerCP using a lyse no-wash sample preparation. Scatter was obtained using a red diode laser as laser 122 described above. The scatter signal was used to trigger an illumination pulse from the blue (470 nm) LED a few microseconds after the scatter measurement. Fluorescence of PerCP was excited by the LED and measured with a 680/40 band pass filter.

EXAMPLE 9

The scatter plots and histograms shown in FIGS. 21A through 23B represent exemplary results obtained with a Nichia blue LED employed as LED 125 for a sperm sample. The sperm staining reagent was SYTO 16+Ethidium homodimer+FACSCount counting beads in FACSpets.

EXAMPLE 10

The scatter plots shown in FIGS. 24A through 25B represent exemplary results obtained with a blue LED employed as LED 125 in an arrangement according to the embodiments described above.

EXAMPLE 11

The scatter plots and histograms shown in FIGS. 26A through 28B represent exemplary results obtained for a sample of Ethanol-fixed T47D cells stained with DAPI and analyzed with a UV LED employed as LED 125 in an arrangement according to the embodiments of the invention described above. FL1-H is the pulse height signal from a narrow slit associated with a detector designated as FL1, and FL1-A is the pulse area signal from a tall slit associated with detector FL1, using a slit panel as described above with reference to FIGS. 8 and 9.

EXAMPLE 12

The scatter plots and histograms shown in FIGS. 29A through 29D represent exemplary results obtained for a cell sample stained with FL1-FITC, FL3-UV DNA stain and analyzed with a UV LED employed as LED 125 in an arrangement according to the embodiments of the invention described above. A 488 nm argon ion laser was sued to excite FITC fluorescence. FL1 and FL3 are designations given to respective detectors.

Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims.

What is claimed is:

1. An apparatus for examining a particle in a flow stream of a flow cytometer, comprising:

a light emitting device comprising at least one incoherent light emitting semiconductor device, adapted to emit light toward said flow stream;

a detector, adapted to detect light emanating from said particle in response to said emitted light striking said particle; and a light obstructing device, having a substantially opaque portion which is adapted to prevent a portion of said emanating light from being detected by said detector, and at least two substantially transparent portions which are adapted to permit another portion of said emanating light to pass to said detector for detection by said detector;

wherein one of said transparent portions of said light obstructing device is larger than the other of said transparent portions.

2. An apparatus for examining a particle in a flow stream of a flow cytometer, comprising:

a light emitting device comprising at least one light emitting diode, adapted to emit light toward said flow stream;

a detector, adapted to detect light emanating from said particle in response to said emitted light striking said particle;

a controller, adapted to control said light emitting diode to emit said emitted light in pulses; and a light obstructing device, having a substantially opaque portion which is adapted to prevent a portion of said emanating light from being detected by said detector, and at least two substantially transparent portions which are adapted to permit another portion of said emanating light to pass to said detector for detection by said detector;

wherein one of said transparent portions of said light obstructing device is larger than the other of said transparent portions.

* * * * *